US010028665B2

(12) United States Patent
Fernando et al.

(10) Patent No.: US 10,028,665 B2
(45) Date of Patent: Jul. 24, 2018

(54) BIOSIGNAL DETERMINING DEVICE AND BIOSIGNAL DETERMINING METHOD

(71) Applicant: Panasonic Intellectual Property Management Co., Ltd., Osaka (JP)

(72) Inventors: Jeffry Bonar Fernando, Osaka (JP); Jun Ozawa, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 419 days.

(21) Appl. No.: 14/843,490

(22) Filed: Sep. 2, 2015

(65) Prior Publication Data
US 2016/0073906 A1    Mar. 17, 2016

(30) Foreign Application Priority Data

Sep. 12, 2014   (JP) ................. 2014-186626

(51) Int. Cl.
*A61B 5/02*     (2006.01)
*A61B 5/0205*   (2006.01)
(Continued)

(52) U.S. Cl.
CPC .......... *A61B 5/0205* (2013.01); *A61B 5/0402* (2013.01); *A61B 5/0408* (2013.01); *A61B 5/0809* (2013.01); *A61B 5/74* (2013.01)

(58) Field of Classification Search
CPC ... A61B 5/0402; A61B 5/0408; A61B 5/0809; A61B 5/74; A61B 5/0205
See application file for complete search history.

(56) References Cited

U.S. PATENT DOCUMENTS 4,984,158 A * 1/1991 Hillsman ............... A61B 5/087
128/200.14
7,371,220 B1 * 5/2008 Koh ..................... A61B 5/0809
600/529
(Continued)

FOREIGN PATENT DOCUMENTS

JP    63-502563    9/1988
JP    2007-229101    9/2007
(Continued)

OTHER PUBLICATIONS

Jeffry Bonar Fernando et al., "Estimation of respiratory signal from thoracic impedance cardiography in low electrical current", International Conference of the IEEE Engineering in Medicine and Biology Society, pp. 3829-3832 (2013).
(Continued)

*Primary Examiner* — Navin Natnithithadha
*Assistant Examiner* — Eric Messersmith
(74) *Attorney, Agent, or Firm* — Wenderoth, Lind & Ponack, L.L.P.

(57) ABSTRACT

A biosignal determining device includes: an instruction output circuit which outputs a first instruction, a second instruction, and a third instruction to a user, the first instruction is for asking the user to perform an inhaling or exhaling motion to a limit, a second instruction is for asking the user to stop the motion, and a third instruction is for asking the user to perform a motion reverse to the motion to a limit; a detection circuit which obtains a first cardiography representing a potential difference between two electrodes disposed on a chest of the user, the first cardiography measured between a time when the second instruction is outputted and a time when the third instruction is outputted, and detects a plurality of peaks included in the first cardiography; and a determination circuit which determines whether the user has performed the motion asked in the first instruction to the
(Continued)

limit depending on whether potential values of the plurality of peaks are included in a predetermined range.

13 Claims, 31 Drawing Sheets

(51) Int. Cl.
*A61B 5/0408* (2006.01)
*A61B 5/08* (2006.01)
*A61B 5/00* (2006.01)
*A61B 5/0402* (2006.01)

(56) References Cited

U.S. PATENT DOCUMENTS

| | | | | |
|---|---|---|---|---|
| 2010/0217133 | A1* | 8/2010 | Nilsen | A61B 5/0205 600/484 |
| 2012/0029376 | A1* | 2/2012 | Meng | A61B 5/087 600/538 |
| 2012/0041279 | A1* | 2/2012 | Freeman | A61B 5/0205 600/301 |
| 2015/0258370 | A1* | 9/2015 | Arkush | A61B 5/087 482/8 |
| 2015/0342518 | A1* | 12/2015 | Persidsky | A61B 5/486 600/534 |

FOREIGN PATENT DOCUMENTS

| | | |
|---|---|---|
| JP | 2010-213773 | 9/2010 |
| JP | 2014-050626 | 3/2014 |
| WO | 1987/004332 | 7/1987 |

OTHER PUBLICATIONS

Baldwin, E. D et al., "Pulmonary insufficiency: I. Physiological classification, clinical methods of analysis, standard values in normal subjects", Medicine, 27, p. 243-278 (1948).

* cited by examiner

FIG. 4A

|  | AVERAGE AMPLITUDE IN NORMAL BREATHING [$\mu$V] | AVERAGE AMPLITUDE IN DEEP BREATHING [$\mu$V] |
|---|---|---|
| SUBJECT 1 | 6.15 | 12.43 |
| SUBJECT 2 | 20.12 | 47.90 |

FIG. 4B

| | | AVERAGE AMPLITUDE IN NORMAL BREATHING [$\mu$V] | AVERAGE AMPLITUDE IN DEEP BREATHING [$\mu$V] |
|---|---|---|---|
| POSTURE | SITTING | 7.11 | 19.27 |
| | STANDING | 14.98 | 25.12 |
| | LYING | 26.02 | 43.15 |

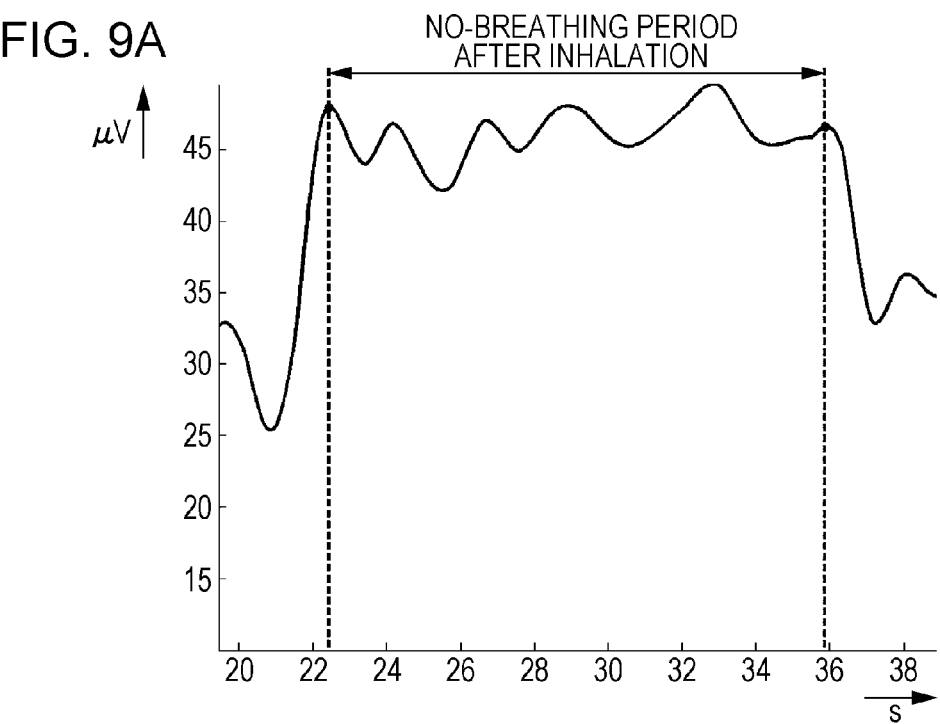
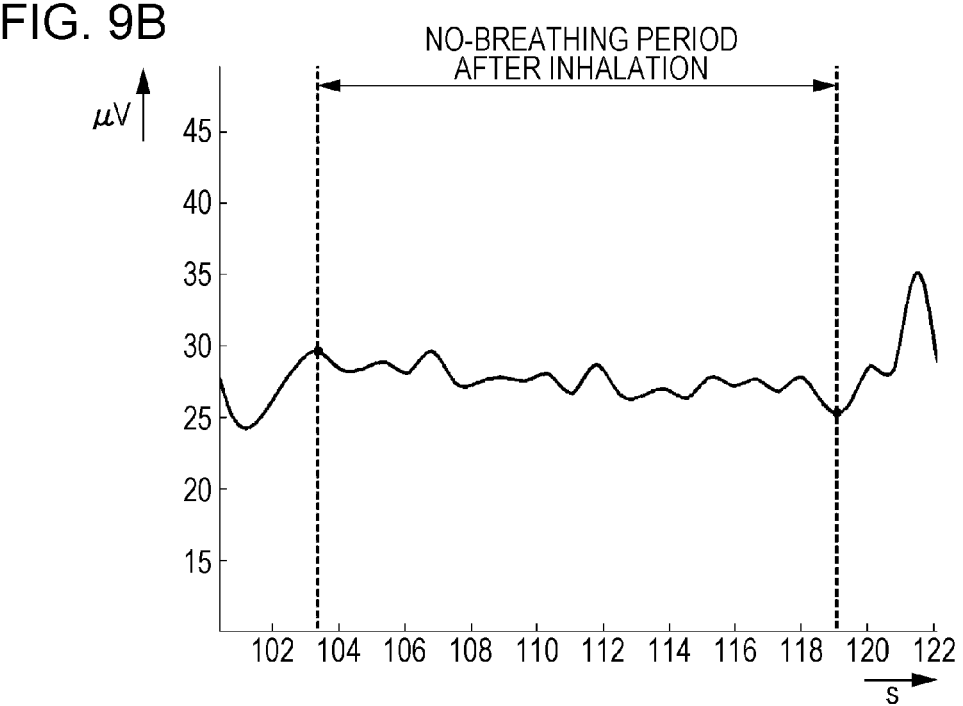

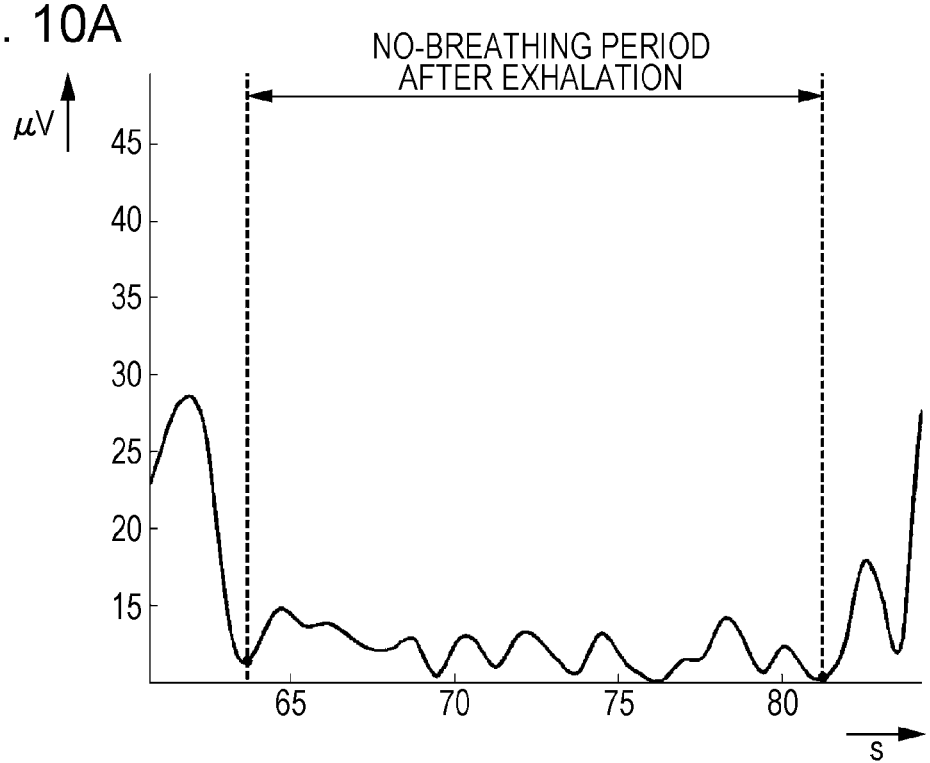
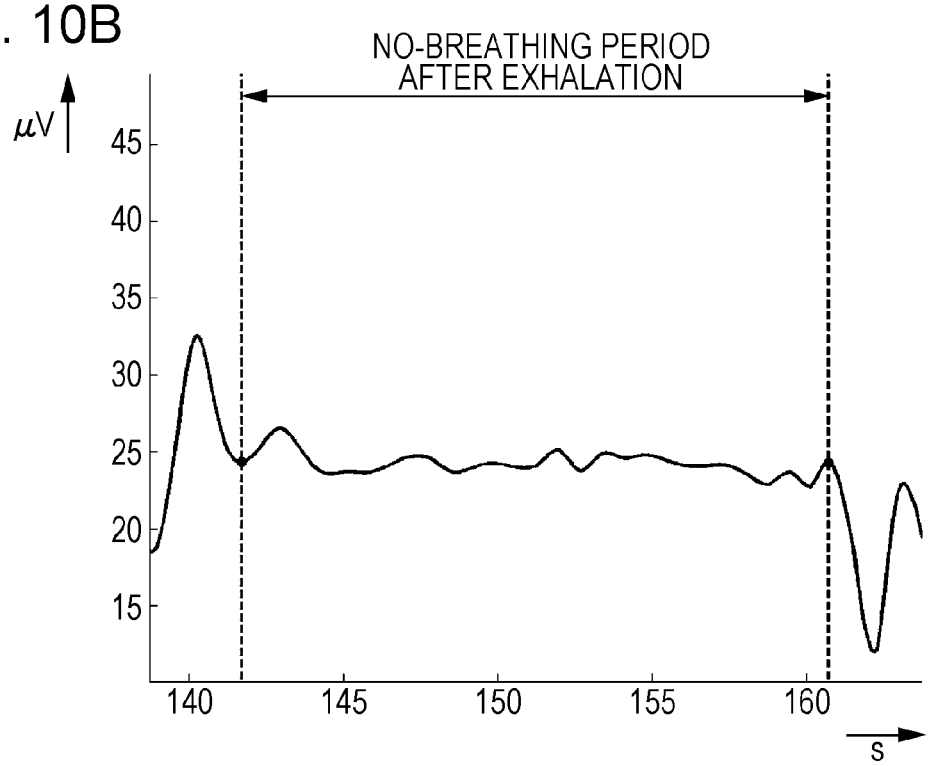

FIG. 14A

|  | STANDARD DEVIATION IN NO BREATHING [μV] |
|---|---|
| FULL INHALATION | 2.18 |
| HALFWAY INHALATION | 0.61 |

FIG. 14B

|  | STANDARD DEVIATION IN NO BREATHING [μV] |
|---|---|
| FULL EXHALATION | 1.80 |
| HALFWAY EXHALATION | 0.67 |

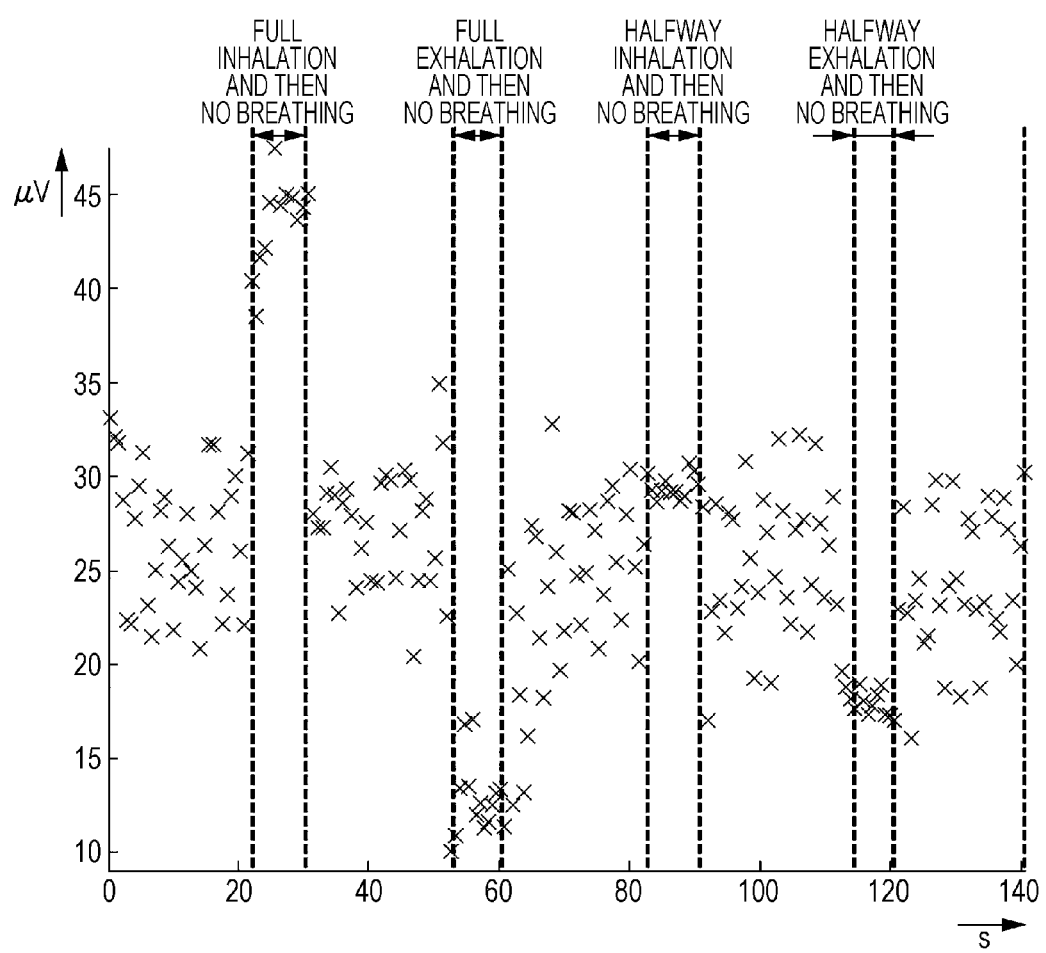

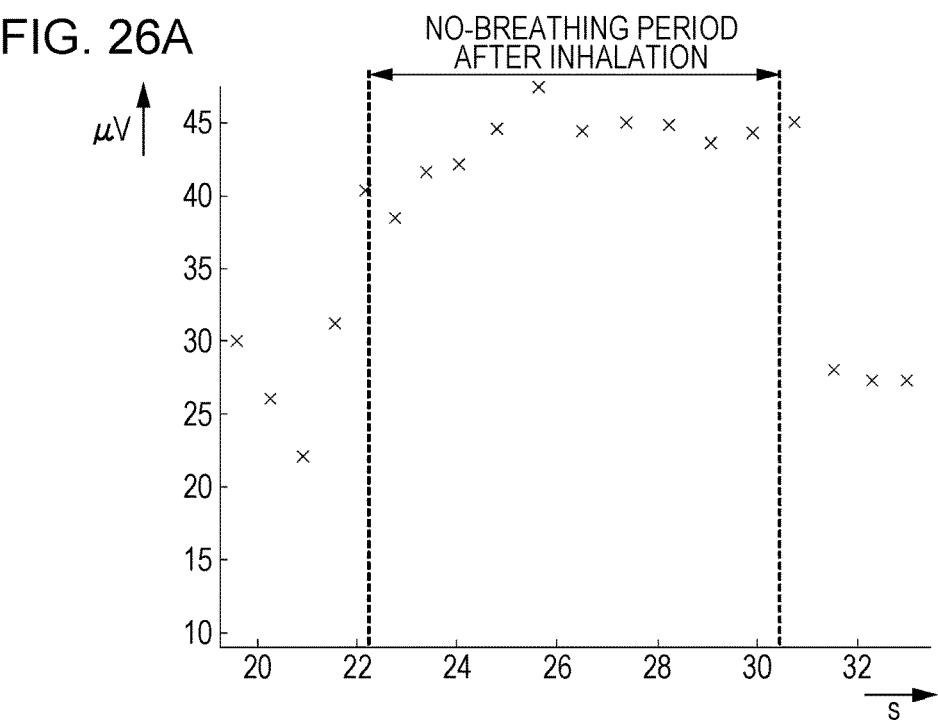
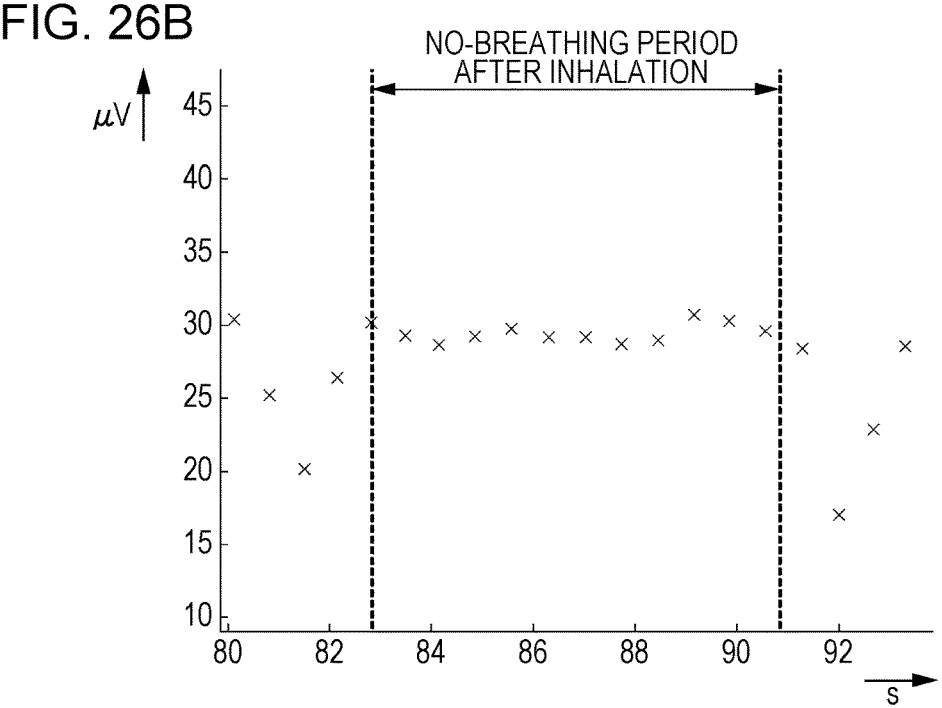

FIG. 28A

| | STANDARD DEVIATION IN NO BREATHING [$\mu V$] |
|---|---|
| FULL INHALATION | 2.42 |
| HALFWAY INHALATION | 0.64 |

FIG. 28B

| | STANDARD DEVIATION IN NO BREATHING [$\mu V$] |
|---|---|
| FULL EXHALATION | 1.95 |
| HALFWAY EXHALATION | 0.69 |

BIOSIGNAL DETERMINING DEVICE AND BIOSIGNAL DETERMINING METHOD

BACKGROUND

1. Technical Field

The present disclosure relates to a biosignal determining device and biosignal determining method for measuring biological impedance by using a plurality of electrodes attached onto the body of a user and for extracting information regarding respiration.

2. Description of the Related Art

A method of extracting respiratory information from thoracic impedance in low electrical current (10 nA) is disclosed in Jeffry Bonar Fernando, et al., "Estimation of respiratory signal from thoracic impedance cardiography in low electrical current", International Conference of the IEEE Engineering in Medicine and Biology Society, pp. 3829-3832 (2013).

Prior to describing the concept of the method described in the above cited document "Estimation of respiratory signal from thoracic impedance cardiography in low electrical current", basic components of cardiography are described. FIG. 1 depicts basic components of cardiography in one cycle. The cardiography has peaks called a P wave, a Q wave, an R wave, an S wave, and a T wave. A portion of each of QRS waves represents excitation of the ventricles.

FIG. 2A to FIG. 2C represent a concept of the method described in the above cited document "Estimation of respiratory signal from thoracic impedance cardiography in low electrical current". At measurement, four electrodes are attached onto the center of the chest (refer to FIG. 2A). In FIG. 2A, except an electrode to establish a ground, inner two of four electrodes in line are used to measure a potential. Between two outer electrodes, a low electrical current (10 nA) is caused to flow. FIG. 2B depicts thoracic impedance measured from the potential. In the above cited document "Estimation of respiratory signal from thoracic impedance cardiography in low electrical current", the envelope of the T wave as a cardiography-derived component is referred to as a respiration curve, and the respiration curve is assumed to include respiratory information.

In the above cited document "Estimation of respiratory signal from thoracic impedance cardiography in low electrical current", thoracic impedance is measured by attaching four electrodes onto the center of the chest. In an experiment described in the above cited document "Estimation of respiratory signal from thoracic impedance cardiography in low electrical current", a subject was made to perform breathing in four phases, that is, "normal breathing", "deep breathing", "no breathing", and then "normal breathing". The subject was instructed to perform normal breathing in a cycle of three seconds fifteen times, perform deep breathing in a cycle of five seconds eight times, and stop breathing for thirty seconds.

FIG. 2C depicts respiration extraction results. The cycle in the envelope is correlated with actual breathing. Since the amplitude in no breathing is extremely small and the amplitude in deep breathing is larger than the amplitude in normal breathing, the extracted respiratory information represents actual breathing.

SUMMARY

In the above-described related art, it is desired to improve technology for more accurately extracting respiration. One non-limiting and exemplary embodiment provides a technology for more accurately extracting respiration.

In one general aspect, the techniques disclosed here feature a biosignal determining device including: an instruction output circuit which outputs a first instruction, a second instruction, and a third instruction in this order to a user, the first instruction, the second instruction, and the third instruction are outputted in this order, the first instruction is for asking the user to perform an inhaling or exhaling motion to a limit, the second instruction is for asking the user to stop the motion, and the third instruction is for asking the user to perform a motion reverse to the motion to a limit; a detection circuit which obtains a first cardiography representing a potential difference between two electrodes disposed on a chest of the user, the first cardiography measured between a time when the second instruction is outputted and a time when the third instruction is outputted, and detects a plurality of peaks included in the first cardiography; and a determination circuit which determines whether the user has performed the motion asked in the first instruction to the limit depending on whether potential values of the plurality of peaks are included in a predetermined range.

According to the biosignal determining device of an aspect of the present disclosure, it is possible to determine whether the user has fully inhaled and fully exhaled. If the user has not fully inhaled or fully exhaled, it is possible to instruct the user to perform again.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 4A is a diagram of an average amplitude of a respiration curve in normal breathing and an average amplitude of a respiration curve in deep breathing for each subject;

FIG. 4B is a diagram of average amplitudes in normal breathing and deep breathing in each posture;

FIG. 9A is a diagram schematically depicting, in an enlarged manner, a period in the respiration curve in which a user fully inhales and then does not breathe;

FIG. 9B is a diagram schematically depicting, in an enlarged manner, a period in the respiration curve in which the user halfway inhales and then does not breathe;

FIG. 10A is a diagram schematically depicting, in an enlarged manner, a period in the respiration curve in which the user fully exhales and then does not breathe;

FIG. 10B is a diagram schematically depicting, in an enlarged manner, a period in the respiration curve in which the user halfway exhales and then does not breathe;

FIG. 14A is a diagram of standard deviations during the no-breathing period in the respiration curve depicted in FIG. 12A and FIG. 12B;

FIG. 14B is a diagram of standard deviations during the no-breathing period in the respiration curve depicted in FIG. 13A and FIG. 13B;

FIG. 25 is a diagram of obtained respiratory information;

FIG. 26A is a diagram schematically depicting, in an enlarged manner, a period in the respiratory information in which a user fully inhales and then does not breathe;

FIG. 26B is a diagram schematically depicting, in an enlarged manner, a period in the respiratory information in which the user halfway inhales and then does not breathe;

FIG. 28A is a diagram of standard deviations during the no-breathing period in the respiration curve depicted in FIG. 26A and FIG. 26B;

FIG. 28B is a diagram of standard deviations during the no-breathing period in the respiration curve depicted in FIG. 27A and FIG. 27B;

DETAILED DESCRIPTION (Knowledge from Experiments)

Firstly, knowledge obtained by the inventors performing experiments is described. Note that a "respiration curve" in the following description of the experiments represents an envelope of T-wave peaks in cardiography.

Figure 3:
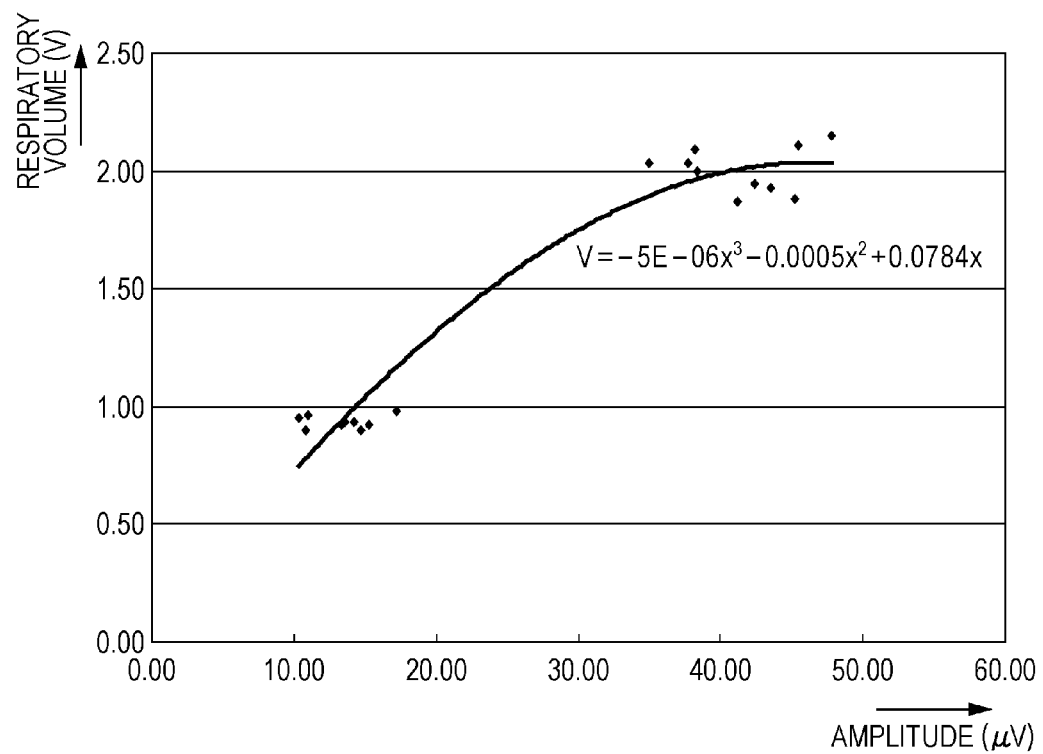
FIG. 3 is a graph of amplitudes of a respiration curve with respect to respiratory volumes.

The amplitude of the respiration curve extracted from thoracic impedance is proportional to respiratory volume. The respiratory volume varies typically depending on the type of breathing (for example, no breathing, normal breathing, or deep breathing). Therefore, the respiratory volume or the type of breathing (no breathing, normal breathing, or deep breathing) can be estimated from the amplitude of the respiration curve. The inventors of the present disclosure have measured thoracic impedance of a subject and also measured respiratory volume by putting a mask on the mouth of the subject and using a respiratory metabolism measurement device. FIG. 3 depicts a graph of amplitudes of a respiration curve with respect to respiratory volumes. FIG. 3 is a plot of measurement values of the respiratory volume and amplitude. In FIG. 3, a solid line represents an approximate curve obtained based on each point. FIG. 3 also depicts an approximate curve by a cubic curve represented in Equation 1.

$$V = -5 \times 10-6 \, Amp_3 - 0.0005 \, Amp_2 + 0.0784 \, Amp \quad \text{(Equation 1)}$$

where V represents respiratory volume and Amp represents amplitude.

By using a conversion formula from amplitude to respiratory volume, a respiratory volume can be estimated from the amplitude of the respiration curve obtained by measurement.

The inventors have set a hypothesis that the amplitude of the respiration curve differs for each person and have tried its verification. If this hypothesis is correct, it can be said that it is difficult to uniformly define an amplitude-respiratory volume conversion formula.

The inventors of the present disclosure have measured thoracic impedance of two subjects in low electrical current (10 nA), and made each subject perform normal breathing and deep breathing. To make the subjects perform breathing with an approximately same respiratory volume, the inventors of the present disclosure have made each subject perform normal breathing in a cycle of two seconds and deep breathing in a cycle of four seconds. By using the method described in Baldwin, E. D., Cournand, A., and Richards, D. W., Jr., "Pulmonary insufficiency: I. Physiological classification, clinical methods of analysis, standard values in normal subjects", Medicine, 27, pp. 243-278 (1948), the inventors of the present disclosure have extracted a respiration curve from the thoracic impedance and found the amplitude of the respiration curve in each of normal breathing and deep breathing.

FIG. 4A depicts an average amplitude of a respiration curve in normal breathing and an average amplitude of a respiration curve in deep breathing for each subject. The amplitude of the respiration curve in normal breathing of a subject 1 is 6.15 µV, and the amplitude of the respiration curve in deep breathing of the subject 1 is 12.43 µV. By contrast, the amplitude of the respiration curve in normal breathing of a subject 2 is 20.12 µV, and the amplitude of the respiration curve in deep breathing of the subject 2 is 47.90 µV. The amplitude of the subject 2 is three times as much as the amplitude of the subject 1 or more, even with an approximately same respiratory volume. Therefore, it can be said that it is difficult to uniformly define an amplitude-respiratory volume conversion formula.

Furthermore, the inventors of the present disclosure have thought that the amplitude of the respiration curve varies with different postures when impedance is measured, even with the same person, and have tried verification. If this hypothesis is correct, this also means that it is difficult to uniformly define an amplitude-respiratory volume conversion formula, even with the same person.

The inventors have made the subject 1 take three postures, that is, "sitting", "standing", and "lying". The inventors have made the subject 1 perform normal breathing and deep breathing in each posture, and measured thoracic impedance of the subject 1 at low electrical current (10 nA). Similarly to the case described above, by using the method described in the above cited document "Pulmonary insufficiency: I. Physiological classification, clinical methods of analysis, standard values in normal subjects", the inventors of the present disclosure have extracted a respiration curve from the thoracic impedance and found the amplitude of each of normal breathing and deep breathing.

FIG. 4B depicts average amplitudes in normal breathing and deep breathing in each posture. In the "sitting" posture, the amplitude of the respiration curve in normal breathing is 7.11 µV and the amplitude of the respiration curve in deep breathing is 19.27 µV. The amplitudes in the "standing" posture are 14.98 µV and 25.12 µV, which are larger than the amplitudes in the "sitting" posture. The amplitudes in the "lying" posture are 26.02 µV and 43.15 µV, which are further larger than the amplitudes in the "sitting" posture. It has been also found that the magnitude of amplitude varies depending on the posture even with an approximately same respiratory volume.

The inventors have obtained knowledge that since the amplitude of the respiration curve varies for each person and posture even with the same respiratory volume, calibration has to be performed to find an amplitude-respiratory volume conversion formula.

Figure 5A:
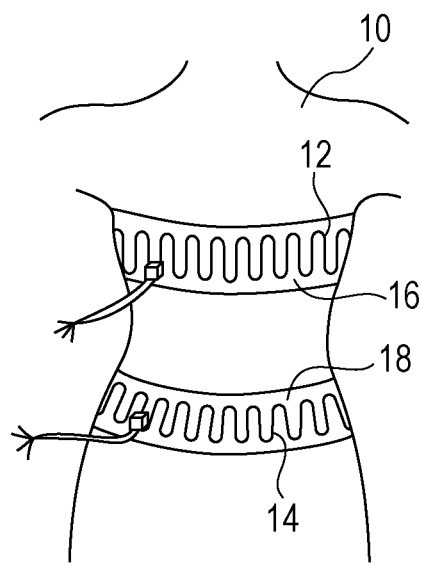
FIG. 5A is a diagram of an example of attaching conductors in a respiration calibrating method described in Japanese Examined Patent Application Publication No. 3-42899.
Figure 5B:
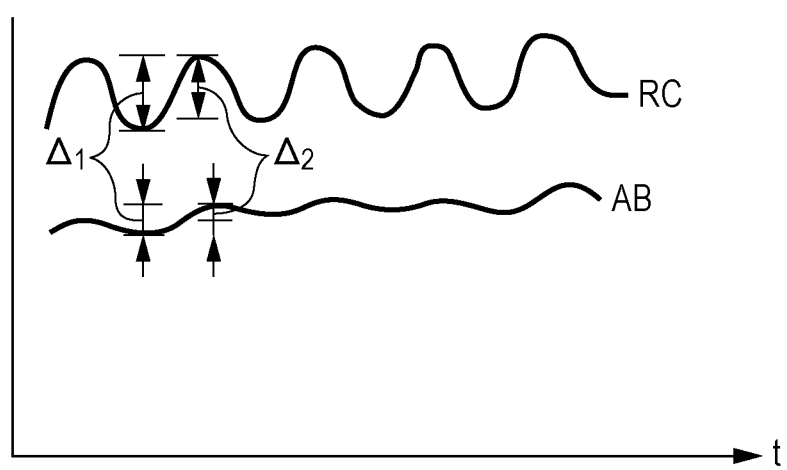
FIG. 5B is a diagram indicating measurement values obtained by the respiration calibrating method described in Japanese Examined Patent Application Publication No. 3-42899.

Japanese Examined Patent Application Publication No. 3-42899 discloses a method of calibrating a formula for calculating a respiratory volume from values in a respiration curve. FIG. 5A and FIG. 5B depict an example of attachment of conductors required in the respiration calibrating method described in Japanese Examined Patent Application Publication No. 3-42899 and measurement values therein, respectively. Conductors 12 and 14 are provided to elastic tubes 16 and 18, respectively, and the elastic tubes 16 and 18 are wound around the rib cage and abdomen, respectively (refer to FIG. 5A). Measurement values of the rib cage conductor 12 and measurement values of the abdomen conductor 14 are represented by RC and AB, respectively (refer to FIG. 5B). To find a respiratory volume (V) from RC and AB, the following Equation 2 is used.

$$V = M \times [(Z \times RC) + AB] \quad \text{(Equation 2)}$$

M and Z are weights. Initially, M and Z are unknowns, and their values are found by calibration. However, for calibration, a spirometer has to be separately provided.

In the above cited document "Pulmonary insufficiency: I. Physiological classification, clinical methods of analysis, standard values in normal subjects", a vital capacity is predicted based on age, gender, and height, by using the following Equation 3.

Male: Predicted vital capacity (mL)=(27.63−
0.112*age)*height (cm)

Female: Predicted vital capacity (mL)=(21.78−
0.101*age)*height (cm)      (Equation 3)

The predicted vital capacity found by Equation 3 can be regarded as a maximum respiratory volume of the user.

By indicating respiration timings to the user so that the user inhales and exhales with the maximum respiratory volume, the amplitude of a respiration curve with the maximum respiratory volume can be obtained. By associating the obtained amplitude and the maximum respiratory volume estimated from Equation 3, it can be thought that an amplitude-respiratory volume conversion formula can be found.

However, a spirometer has to be provided in the technology described in Japanese Examined Patent Application Publication No. 3-42899, thereby, for example, disadvantageously increasing cost and imposing extra work.

To get around this problem, the inventors have studied a method without using a spirometer.

Figure 6:
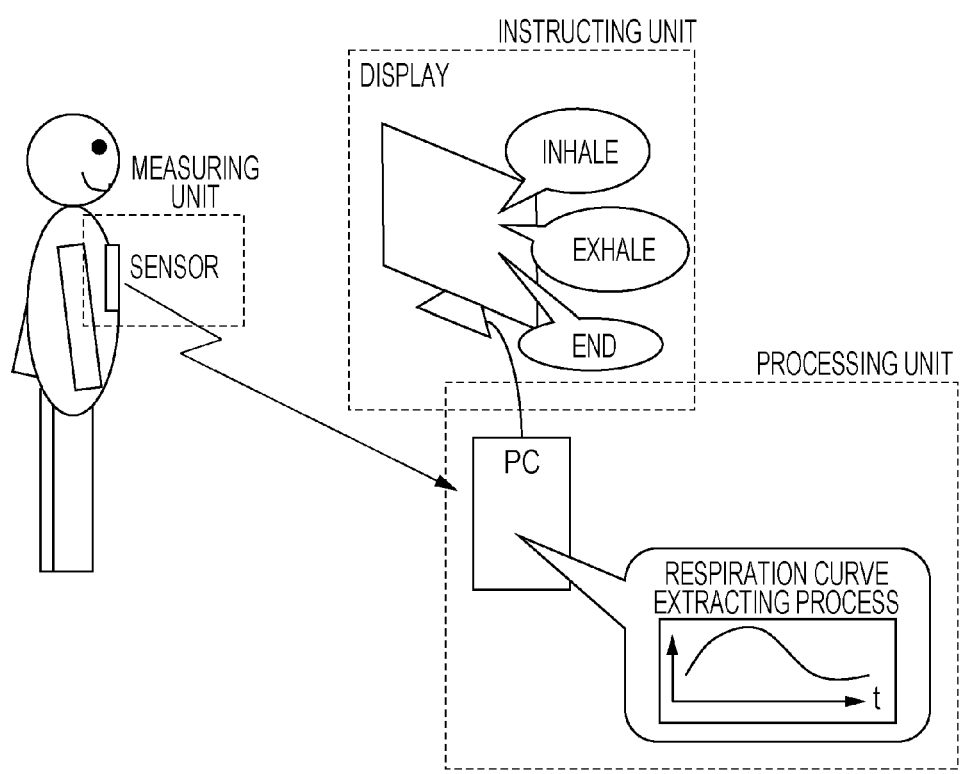
FIG. 6 is a diagram of general outlines of a method of calibrating respiration by indicating respiration timings to a user.

FIG. 6 depicts general outlines of a method of calibrating respiration by indicating respiration timings to a user. A user has attached thereon a sensor for obtaining a respiration curve. The user is instructed to inhale (inhale air) via audio or through a screen. Then, the user is instructed to exhale (exhale air). Finally, the user is notified of process completion. In this manner, the amplitude and respiratory volume can be calibrated without using another device (spirometer).

Figure 7A:
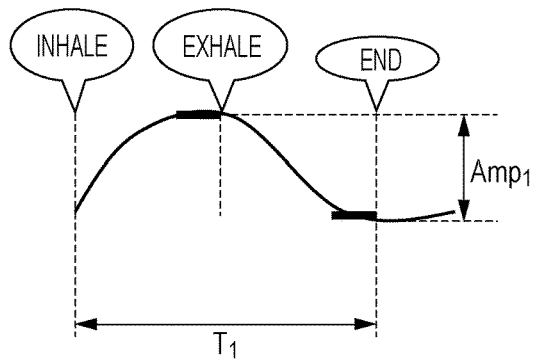
FIG. 7A is a diagram of a method of creating an amplitude-respiratory volume conversion formula.

FIG. 7A to FIG. 7D depict a method of creating an amplitude-respiratory volume conversion formula. FIG. 7A depicts a respiration curve when the user is instructed to breath with a maximum respiratory volume. The amplitude and respiratory cycle at this time are assumed to be $Amp_1$ and $T_1$, respectively. Based on the respiratory cycle $T_1$, a respiratory cycle $T_2$ in a second instruction is set.

For example, T is set by using the following Equation 4.

$$T_2 = \frac{T_1}{2} \quad \text{(Equation 4)}$$

Figure 7B:
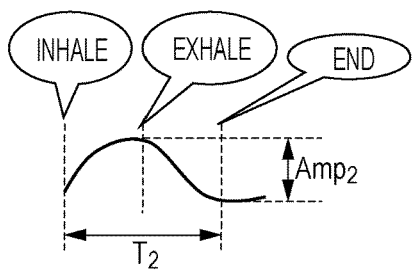
FIG. 7B is a diagram of the method of creating an amplitude-respiratory volume conversion formula.

In the second instruction, inhalation and exhalation timings are indicated so that the respiratory cycle of the user is $T_2$ (refer to FIG. 7B). The amplitude at this time is assumed to be $Amp_2$.

Since the respiratory volume of the user in the first instruction is maximum, this respiratory volume is assumed to be $V_1$, and is found by using Equation 3 mentioned above. The respiratory volume in the second instruction is assumed to be $V_2$ and is found by the following Equation 5.

$$V_2 = f_{TV}\left(\frac{T_2}{T_1}\right) \times V_1 \quad \text{(Equation 5)}$$

Figure 7C:
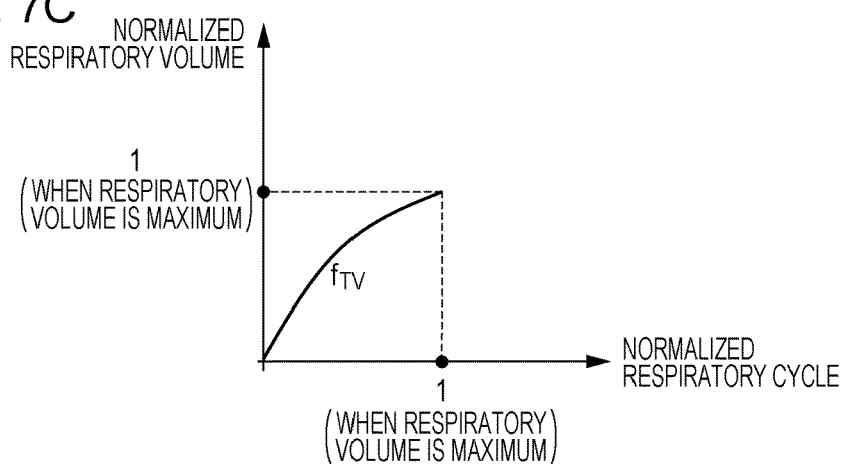
FIG. 7C is a diagram of the method of creating an amplitude-respiratory volume conversion formula.
Figure 7D:
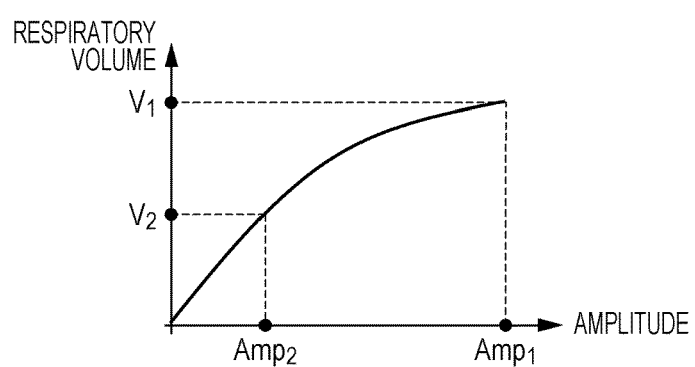
FIG. 7D is a diagram of the method of creating an amplitude-respiratory volume conversion formula.

$f_{TV}$ is a function of a normalized respiratory volume with respect to a normalized respiratory cycle as depicted in FIG. 7C. This function is provided in advance in a database. Since the amplitudes $Amp_1$ and $Amp_2$ and the respiratory volumes $V_1$ and $V_2$ are all provided, an amplitude-respiratory volume conversion formula can be found, as depicted in FIG. 7D.

The inventors of the present disclosure have assessed that the above-described method of using the maximum respiratory volume is preferable as a calibrating method without using a spirometer. To make the method work accurately, the user has to breathe with the maximum respiratory volume.

However, when respiration timings are indicated so that the user inhales and exhales with the maximum respiratory volume, it is unknown whether the user has actually fully inhaled (inhalation limit) and fully exhaled (exhalation limit). Therefore, for proper calibration, whether the user has actually fully inhaled and fully exhaled has to be determined. This is because, if the user has not fully inhaled or fully exhaled, the user has to be instructed to perform calibration again.

Japanese Unexamined Patent Application Publication No. 2010-213773 describes that the user is instructed to perform breathing in synchronization with heart beat. However, there is no description regarding an instruction as to a respiration timing so that the respiratory volume is maximum and determination on whether the user has actually fully inhaled and fully exhaled.

The inventors of the present disclosure have studied how to make a determination on whether the user has actually fully inhaled and fully exhaled.

Firstly, the inventors of the present disclosure have paid attention to characteristics of a respiration curve in no breathing and performed the following experiment. Thoracic impedance of a subject was measured, and a respiratory volume was simultaneously measured by a respiratory metabolism measurement device, with a mask put on the mouth of the subject. The respiratory metabolism measurement device was set so as to output a respiratory volume every ten seconds. In this experiment, the subject was made not breathe for thirty seconds.

Figure 21:
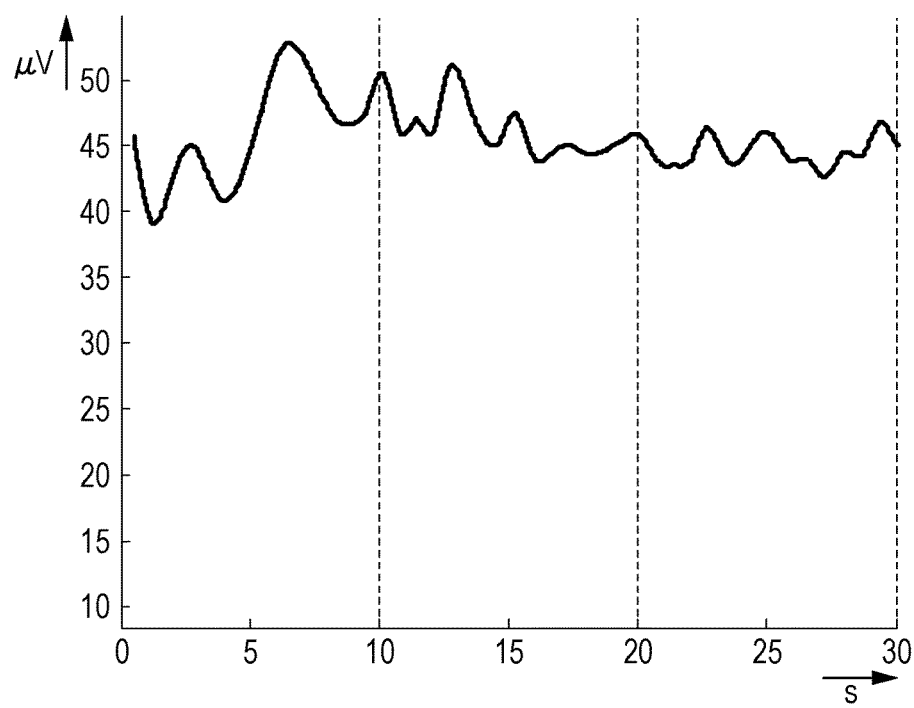
FIG. 21A is a diagram of a respiration curve in no breathing.
FIG. 21B is a diagram of respiratory volumes in no breathing.
Figure 22:
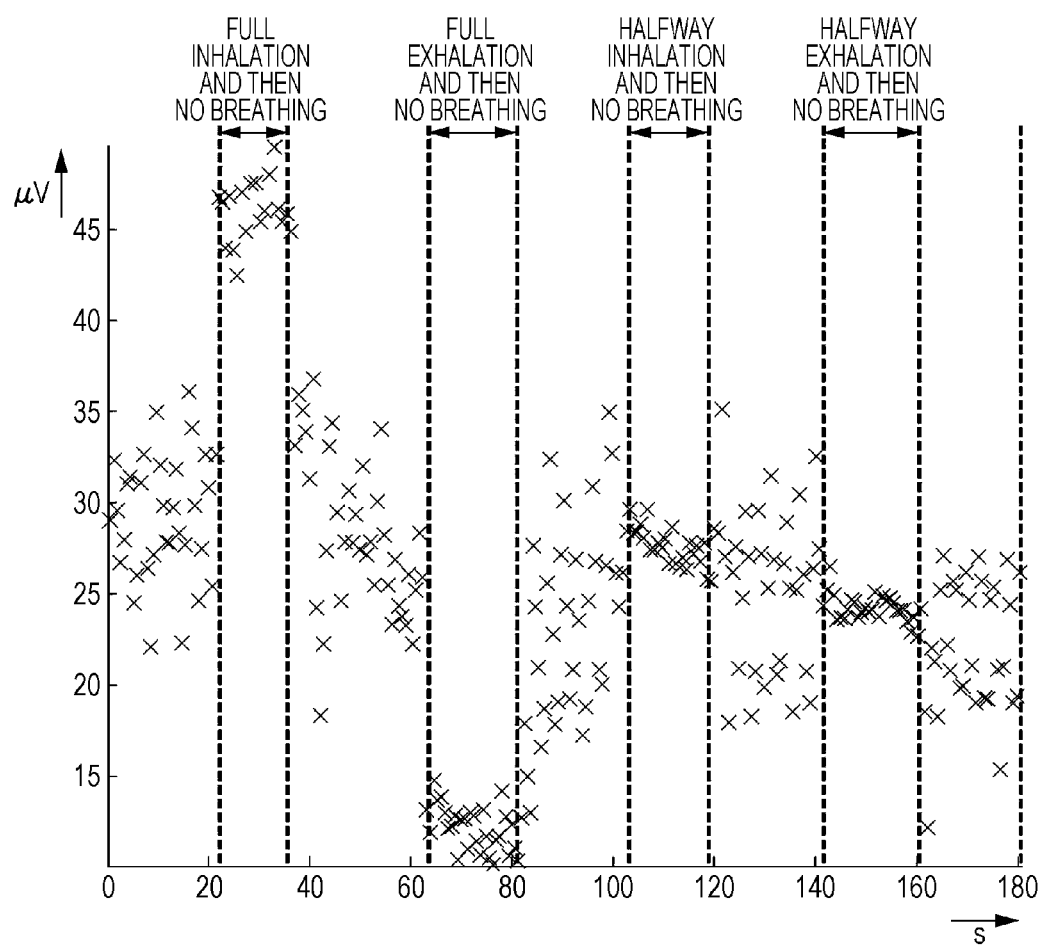
FIG. 22 is a diagram of respiratory information obtained by providing a sensor.

FIG. 21A and FIG. 21B depict the results of the experiment. FIG. 21A depicts a respiration curve extracted from impedance, and FIG. 21B depicts respiratory volumes outputted from the respiratory metabolism measurement device for every ten seconds. Respiratory volumes at 10th second, 20th second, and 30th second are all 0. The respiratory volume of 0 demonstrates that air exchange was not performed through the mask and the subject actually did not breathe. In spite of no breathing, the extracted respiration curve was not constant but fluctuated.

Figure 8:
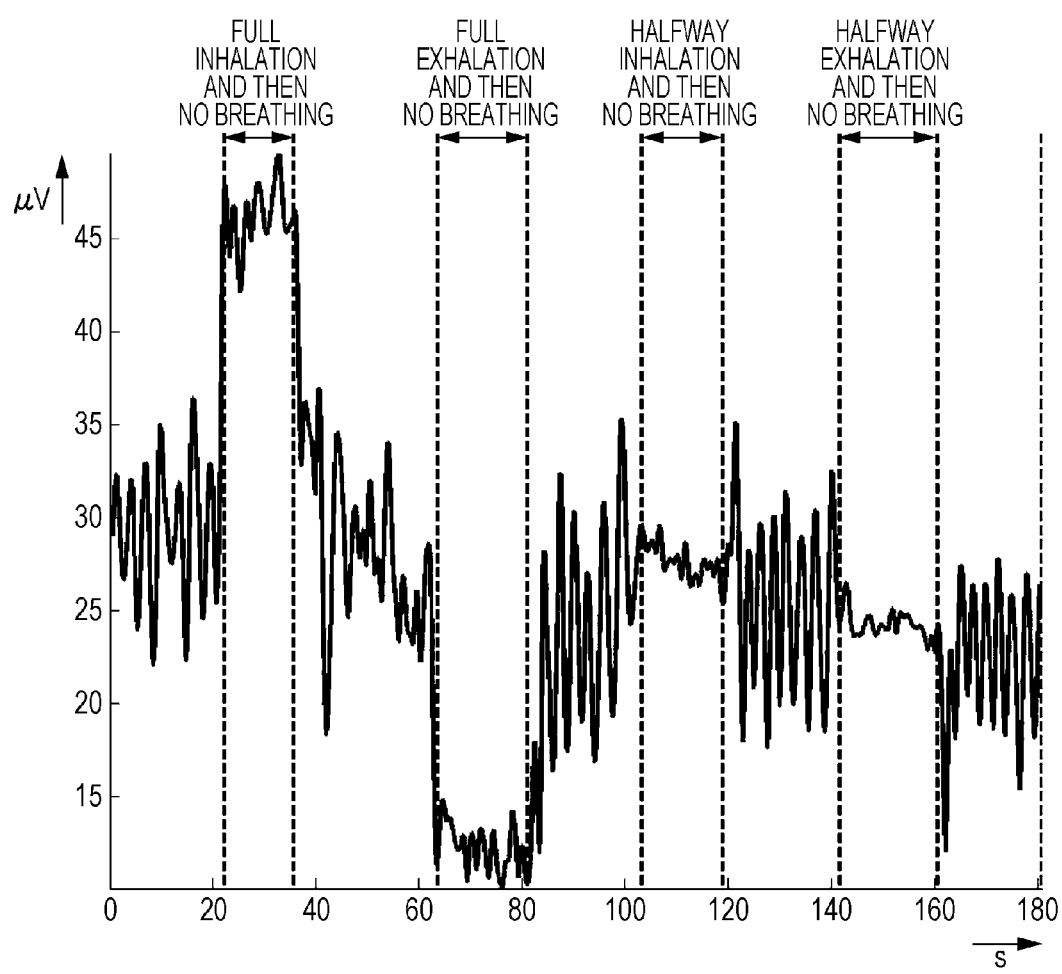
FIG. 8 is a diagram of a respiration curve obtained by providing a sensor.

Next, the inventors of the present disclosure have performed the following experiment. A respiration curve was obtained by providing a sensor to a subject. FIG. 8 depicts the obtained respiration curve. In this experiment, the subject performed breathing in the following manner.

0th second to 21st second: normal breathing
21st second to 36th second: full inhalation and then no breathing
36th second to 62nd second: normal breathing
62nd second to 81st second: full exhalation and then no breathing
81st second to 101st second: normal breathing
101st second to 119th second: halfway inhalation and then no breathing
119th second to 140th second: normal breathing
140th second to 161st second: halfway exhalation and then no breathing
161st second to 180th second: normal breathing FIG. 9A and FIG. 9B schematically depict, in an enlarged manner, a period in the respiration curve in which a user fully inhales and then does not breathe and a period in the respiration curve in which the user halfway inhales and then does not breathe, respectively. In FIG. 9A, the respiration curve falls immediately after the non-breathing period. This is because the user can only exhale after fully inhaling. On the other hand, in FIG. 9B, the respiration curve rises immediately after the non-breathing period. This is because the user inhales after no breathing if the user does not fully inhale before no breathing. Therefore, when the respiration curve rises after the no-breathing period, it can be determined that the user has not fully inhaled.

FIG. 10A and FIG. 10B schematically depict, in an enlarged manner, a period in the respiration curve in which the user fully exhales and then does not breathe and a period in the respiration curve in which the user halfway exhales and then does not breathe, respectively. In FIG. 10A, the respiration curve rises immediately after the non-breathing period. This is because the user can only inhale after fully exhaling. On the other hand, in FIG. 10B, the respiration curve falls immediately after the non-breathing period. This is because the user exhales after no breathing if the user does not fully exhale before no breathing. Therefore, when the respiration curve falls after the no-breathing period, it can be determined that the user has not fully exhaled.

Figure 11:
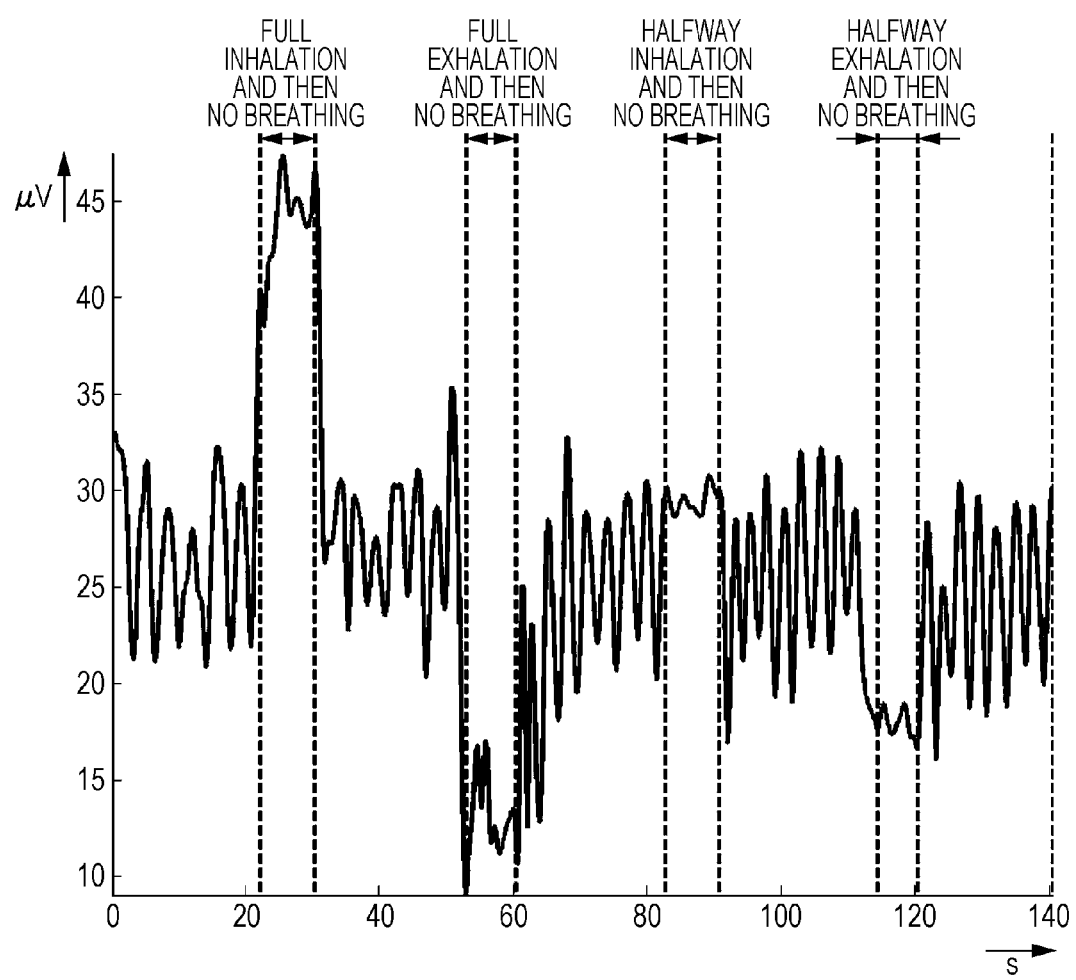
FIG. 11 is a diagram of an obtained respiration curve.

However, when the user halfway inhales and then keeps no breathing, unlike FIG. 9B, there is a possibility that the respiration curve falls after no breathing. Similarly, when the user halfway exhales and then keeps no breathing, unlike FIG. 10B, there is a possibility that the respiration curve rises after no breathing. By using a sensor attached to a subject to again obtain a respiration curve, the inventors of the present disclosure have confirmed cases in which the respiration curve falls after the user halfway inhales and then does not breathe and in which the respiration curve rises after the user halfway exhales and then does not breathe. FIG. 11 depicts the obtained respiration curve. In this experiment, the subject performed breathing in the following manner.

Figure 12A:
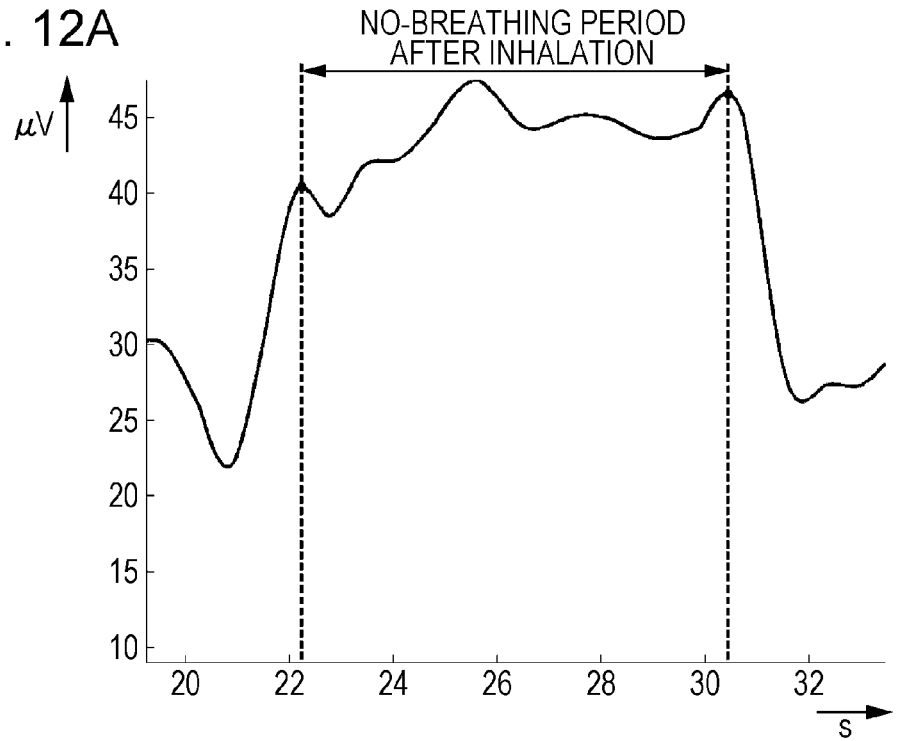
FIG. 12A is a diagram schematically depicting, in an enlarged manner, a period in the respiration curve in which the user fully inhales and then does not breathe.
Figure 12B:
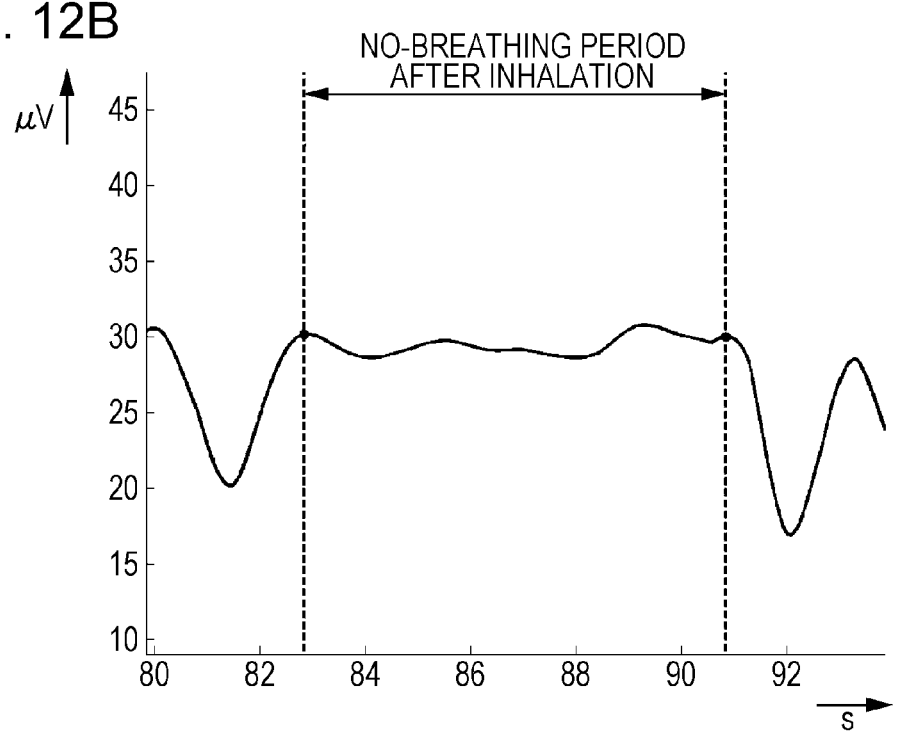
FIG. 12B is a diagram schematically depicting, in an enlarged manner, a period in the respiration curve in which the user halfway inhales and then does not breathe.

0th second to 21st second: normal breathing
21st second to 30th second: full inhalation and then no breathing
30th second to 51st second: normal breathing
51st second to 61st second: full exhalation and then no breathing
61st second to 81st second: normal breathing
81st second to 91st second: halfway inhalation and then no breathing
91st second to 111st second: normal breathing
111st second to 121st second: halfway exhalation and then no breathing
121st second to 140th second: normal breathing FIG. 12A and FIG. 12B schematically depict, in an enlarged manner, a period in the respiration curve in which the user fully inhales and then does not breathe and a period in the respiration curve in which the user halfway inhales and then does not breathe, respectively. In both cases, the respiration curve falls immediately after the no-breathing period ends.

Figure 13A:
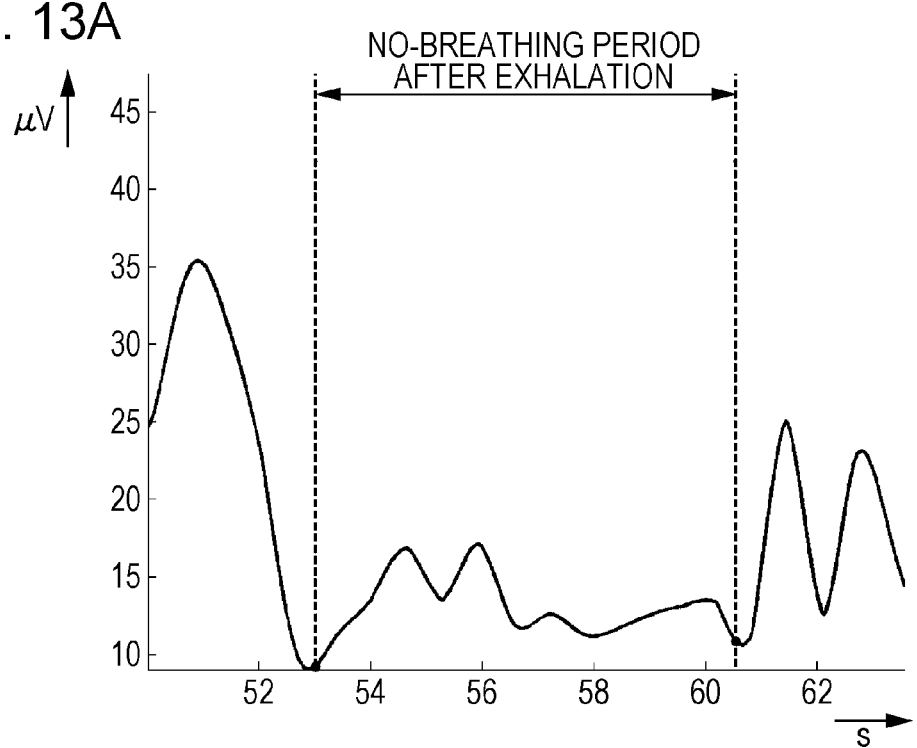
FIG. 13A is a diagram schematically depicting, in an enlarged manner, a period in the respiration curve in which the user fully exhales and then does not breathe.
Figure 13B:
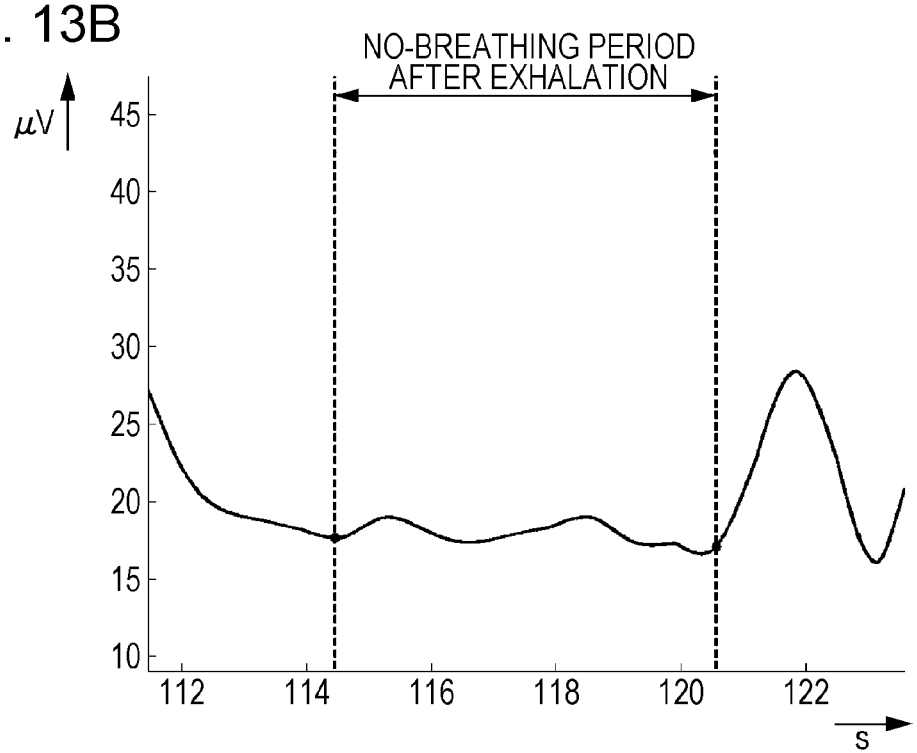
FIG. 13B is a diagram schematically depicting, in an enlarged manner, a period in the respiration curve in which the user halfway exhales and then does not breathe.

FIG. 13A and FIG. 13B schematically depict, in an enlarged manner, a period in the respiration curve in which the user fully exhales and then does not breathe and a period in the respiration curve in which the user halfway exhales and then does not breathe, respectively. In both cases, the respiration curve rises immediately after the no-breathing period ends.

According to FIG. 12A to FIG. 13B, it can be said that it may be difficult to determine, from the respiration curve immediately after the end of the no-breathing period, whether respiration has reached its limit (whether the user has fully inhaled or fully exhaled).

The inventors of the present disclosure have found knowledge capable of determining, from fluctuations of the respiration curve during the no-breathing period, whether respiration has reached its limit, even in this case.

FIG. 14A depicts standard deviation during the no-breathing period in the respiration curve depicted in FIG. 12A and FIG. 12B. FIG. 14B depicts standard deviations during the no-breathing period in the respiration curve depicted in FIG. 13A and FIG. 13B. While the standard deviation in full inhalation is 2.18 µV, the standard deviation in halfway inhalation is 0.61 µV. Similarly, while the standard deviation in full exhalation is 1.80 µV, the standard deviation in halfway exhalation is 0.67 µV. Fluctuations during the no-breathing period in full inhalation or full exhalation are larger than those in halfway inhalation or halfway exhalation.

The reason for large fluctuations in the case of full inhalation or full exhalation can be that if keeping a no-breathing state with respiration reaching its limit, the user becomes suffocated and greatly struggles to breathe. The inventors of the present disclosure have obtained knowledge in which that fluctuations of the respiration curve reflects this struggle.

Furthermore, the inventors of the present disclosure have conceived an approach without using a respiration curve. In Jeffry Bonar Fernando, et al., "Estimation of respiratory signal from thoracic impedance cardiography in low electrical current", International Conference of the IEEE Engineering in Medicine and Biology Society, pp. 3829-3832 (2013), a respiration curve is estimated from a change of measured impedance. That is, the inventors have thought that the change of impedance represents respiratory information and, from the change of impedance, it is supposed to be determined whether the user has fully inhaled or fully exhaled.

In the above cited document "Estimation of respiratory signal from thoracic impedance cardiography in low electrical current", the envelope of the T wave as a cardiography-derived component is taken as respiratory information. That is, a change of the T wave represents respiratory information. Thus, the inventors of the present disclosure have again processed measurement data used in the results of the experiment depicted in FIG. 8 to FIG. 14B. This time, not the respiration curve but time-series T-wave peak values are taken as respiratory information.

FIG. 22 to FIG. 28B depict the process results. Marks x each represent a T-wave peak as a cardiography-derived component in the measured impedance.

Figure 23A:
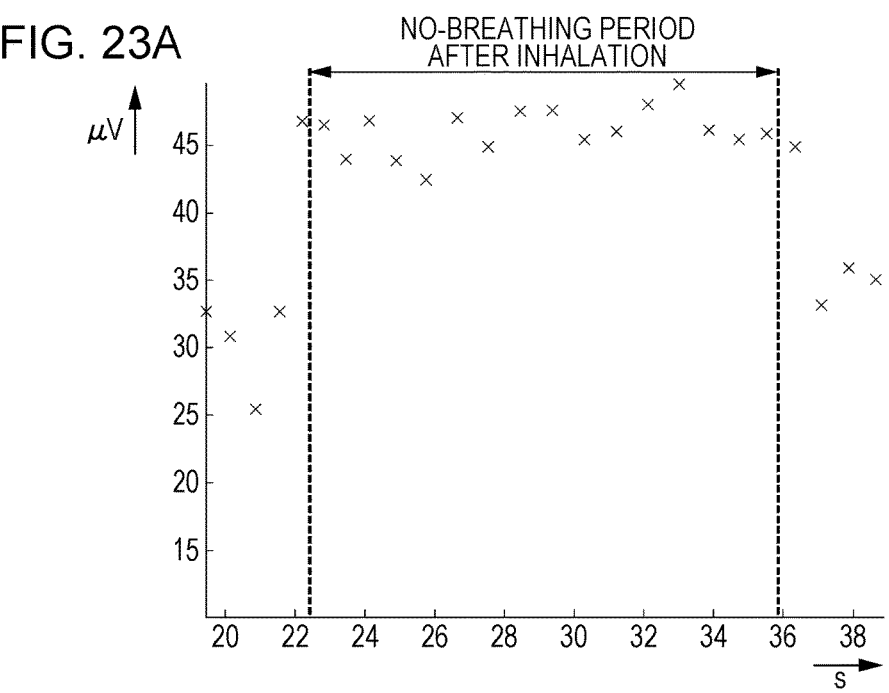
FIG. 23A is a diagram schematically depicting, in an enlarged manner, a period in the respiratory information in which a user fully inhales and then does not breathe.
Figure 23B:
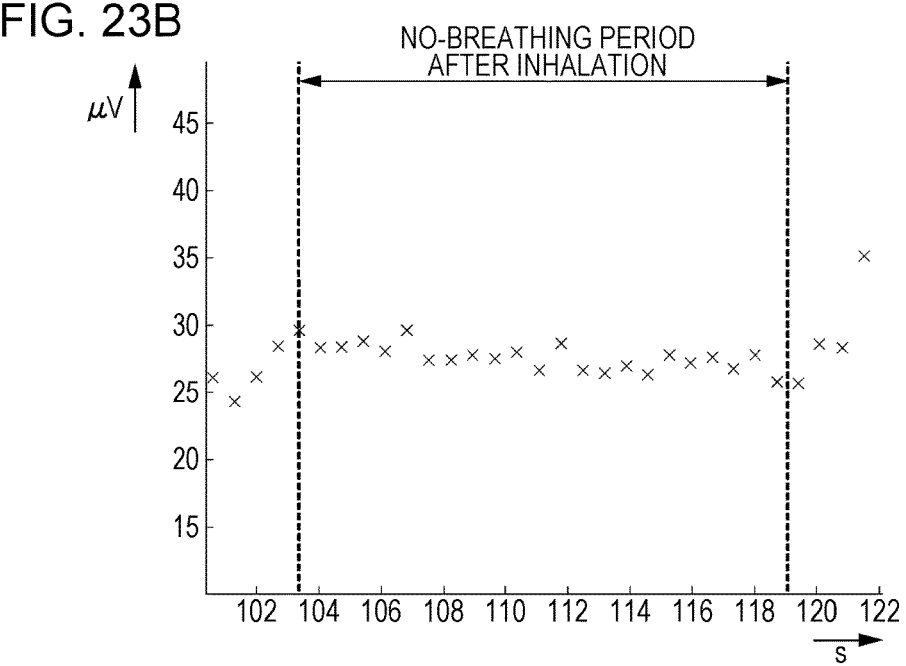
FIG. 23B is a diagram schematically depicting, in an enlarged manner, a period in the respiratory information in which the user halfway inhales and then does not breathe.

In FIG. 23B, immediately after the end of the no-breathing period, a group of T-wave peak points has larger peak values than those of a group of T-wave peak points in no breathing. Therefore, it can be determined that the user has not fully inhaled.

Figure 24A:
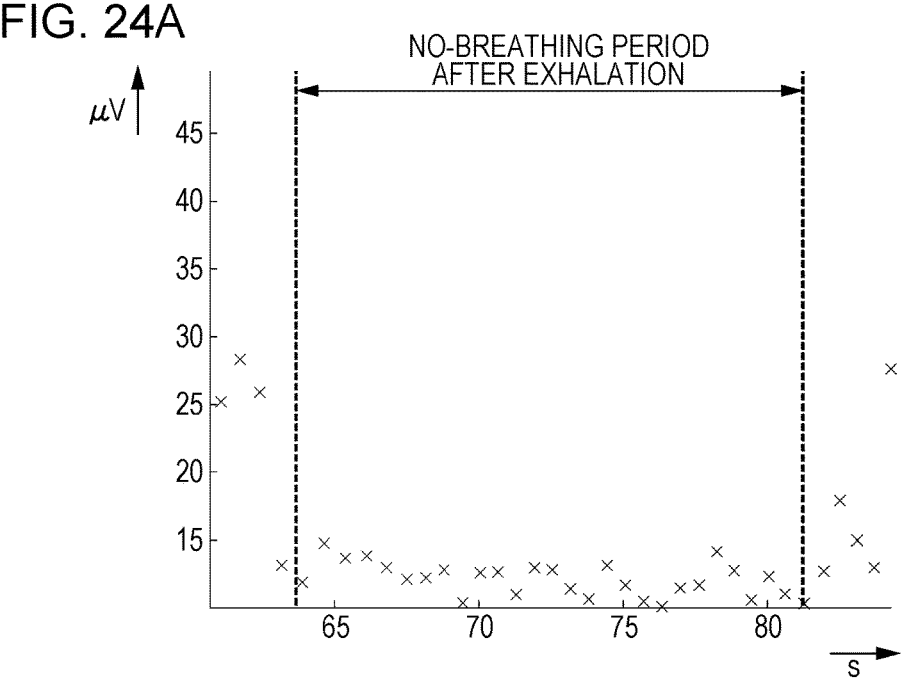
FIG. 24A is a diagram schematically depicting, in an enlarged manner, a period in the respiratory information in which the user fully exhales and then does not breathe.
Figure 24B:
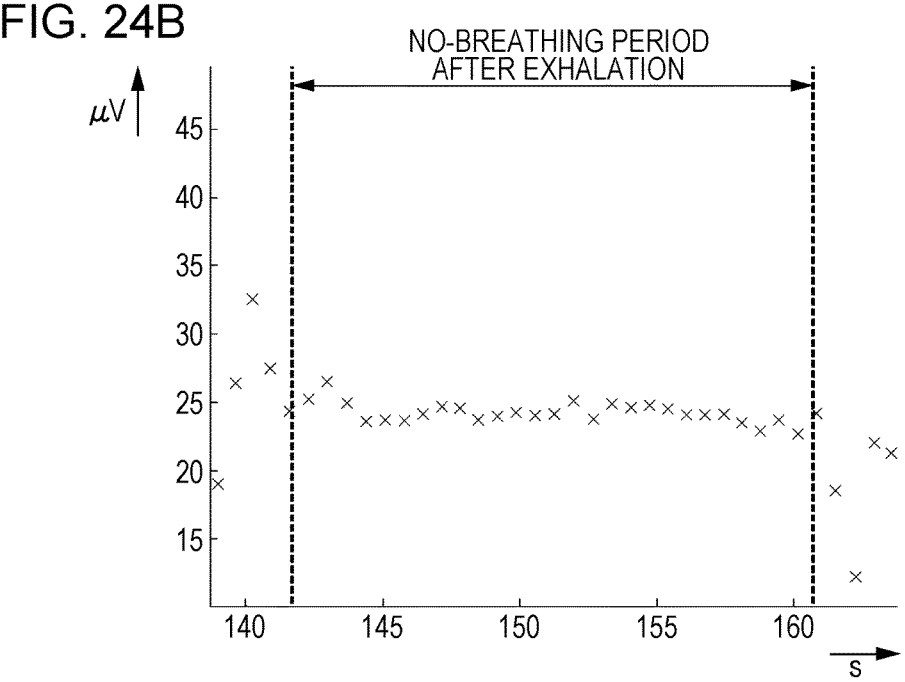
FIG. 24B is a diagram schematically depicting, in an enlarged manner, a period in the respiratory information in which the user halfway exhales and then does not breathe.
Figure 27A:
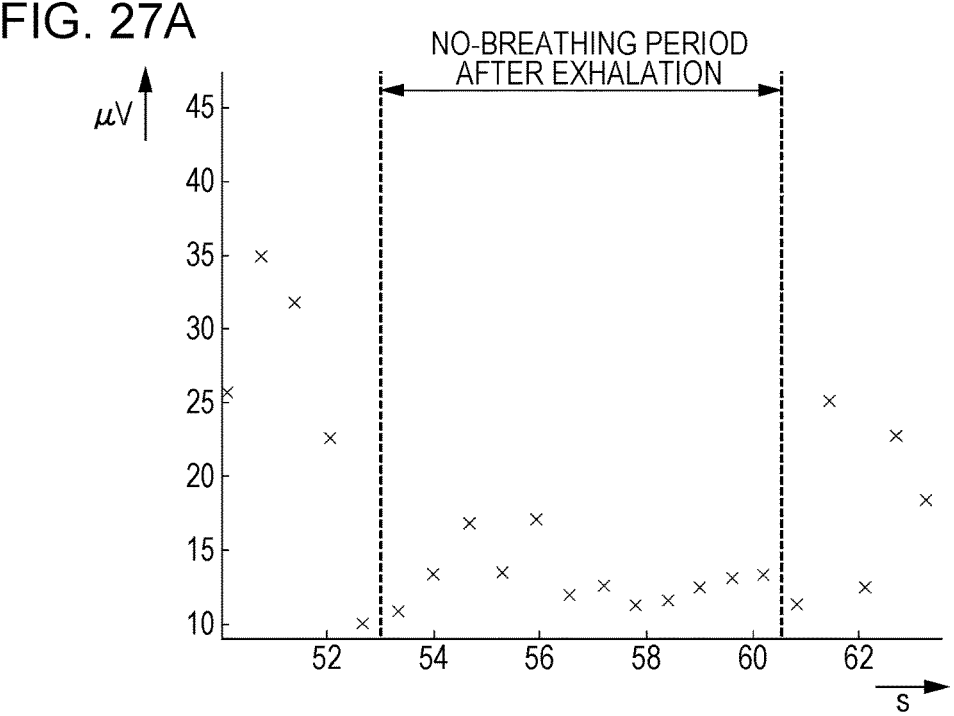
FIG. 27A is a diagram schematically depicting, in an enlarged manner, a period in the respiratory information in which the user fully exhales and then does not breathe.
Figure 27B:
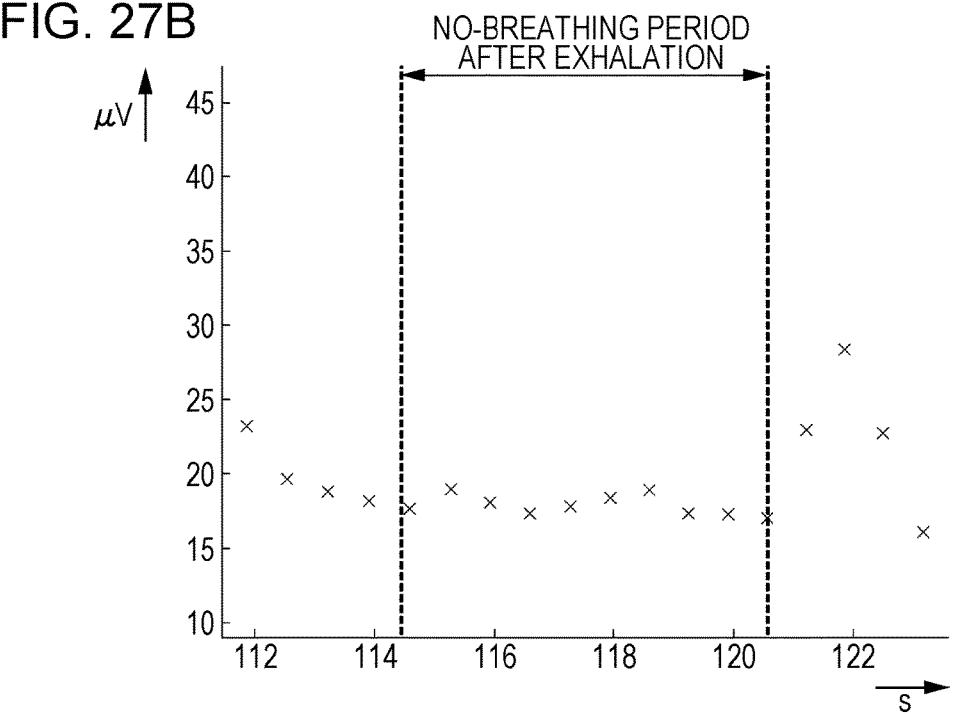
FIG. 27B is a diagram schematically depicting, in an enlarged manner, a period in the respiratory information in which the user halfway exhales and then does not breathe.

In FIG. 24B, immediately after the end of the no-breathing period, a group of T-wave peak points has smaller peak values than those of a group of T-wave peak points in no breathing. Therefore, it can be determined that the user has not fully exhaled.

FIG. 28A depicts standard deviations of a group of T-wave peak points in no breathing in the respiration curve depicted in FIG. 26A and FIG. 26B. FIG. 28B depicts standard deviations of a group of T-wave peak points in no breathing in the respiration curve depicted in FIG. 27A and FIG. 27B. While the standard deviation in full inhalation is 2.42 µV, the standard deviation in halfway inhalation is 0.64 V. Similarly, while the standard deviation in full exhalation is 1.95 µV, the standard deviation in halfway exhalation is 0.69 µV. Fluctuations of the group of T-wave peak points in the no-breathing period in full inhalation or full exhalation are larger than those in halfway inhalation or halfway exhalation.

General outlines of aspects of the present disclosure are as follows.

A biosignal determining device according to an aspect of the present disclosure includes: a detection circuit which obtains information regarding cardiography representing a potential difference between two electrodes disposed on a chest of a user and detects a peak in the cardiography; an instruction output circuit which outputs an instruction to the user, the instruction including a first instruction for asking the user to perform an inhaling or exhaling motion to a limit, a second instruction for asking the user to stop the motion, and a third instruction for asking the user to perform a motion reverse to the motion to a limit; a processing circuit which generates respiratory information regarding respiration of the user in accordance with the third instruction from a peak in the cardiography detected in a time interval starting from a time when the third instruction is outputted; and a determination circuit which determines, from a change in the respiratory information regarding the respiration of the user in accordance with the third instruction, whether the user has performed the motion asked in the first instruction to the limit.

In one embodiment, the instruction output circuit outputs the second instruction after a predetermined time $\Delta T_1$ from a time when the first instruction is outputted.

In one embodiment, the instruction output circuit outputs the third instruction after a predetermined time $\Delta T_2$ from a time when the second instruction is outputted.

In one embodiment, when the instruction output circuit outputs, as the first instruction, an instruction for asking the user to perform the inhaling motion to the limit, the instruction output circuit outputs, as the third instruction, an instruction for asking the user to perform the exhaling motion to the limit.

In one embodiment, when the instruction output circuit outputs, as the first instruction, an instruction for asking the user to perform the exhaling motion to the limit, the instruction output circuit outputs, as the third instruction, an instruction for asking the user to perform the inhaling motion to the limit.

In one embodiment, when the determination circuit determines that the user has not performed the motion asked in the first instruction to the limit, the instruction output circuit again outputs the first instruction.

In one embodiment, the instruction output circuit changes the predetermined time $\Delta T_1$ when outputting the first instruction again.

In one embodiment, the processing circuit generates a respiration curve as respiratory information regarding respiration of the user in accordance with the third instruction by using cardiography starting from a timing when the third instruction is outputted and after a predetermined time $\Delta T_3$.

In one embodiment, the processing circuit further generates respiratory information regarding respiration of the user in accordance with the third instruction from a peak in the cardiography starting from a timing when the second instruction is outputted and after a predetermined time $\Delta T_2$.

In one embodiment, when the instruction output circuit outputs, as the first instruction, an instruction for asking the user to perform the inhaling motion to the limit, if the respiration curve generated by the processing circuit is changed to become large, the determination circuit determines that the user has not performed the motion asked in the first instruction to the limit.

In one embodiment, when the instruction output circuit outputs, as the first instruction, an instruction for asking the user to perform the exhaling motion to the limit, if the respiration curve generated by the processing circuit is changed to become small, the determination circuit determines that the user has not performed the motion asked in the first instruction to the limit.

In one embodiment, when the respiration curve is changed to become small, by further using cardiography starting from a timing when the second instruction is outputted until a time after a predetermined time $\Delta T_2$, the processing circuit generates a respiration curve after the predetermined time $\Delta T_2$ from the timing when the second instruction is outputted, and the determination circuit determines that the user has performed the exhaling motion to the limit when a standard deviation of the respiration curve is equal to or larger than a predetermined threshold, and determines that the user has not performed the exhaling motion to the limit when the standard deviation is smaller than the predetermined threshold.

In one embodiment, when the respiration curve is changed to become large, by further using cardiography starting a timing when the second instruction is outputted until a time after a predetermined time $\Delta T_2$, the processing circuit generates a respiration curve after the predetermined time $\Delta T_2$ from the timing when the second instruction is outputted, and the determination circuit determines that the user has performed the exhaling motion to the limit when a standard deviation of the respiration curve is equal to or larger than a predetermined threshold, and determines that the user has not performed the exhaling motion to the limit when the standard deviation is smaller than the predetermined threshold.

In one embodiment, the processing circuit generates information indicating a respiratory rate of the user by using a peak in the generated respiratory information regarding the respiration of the user in accordance with the third instruction.

In one embodiment, the biosignal determining device further includes a feature extraction circuit which extracts respiratory cycle information and amplitude information from the respiration curve obtained by the processing circuit, an interface device which obtains information regarding gender, age, and height of the user, a respiratory volume estimation circuit which estimates a respiratory volume of the user based on the information obtained by the interface device and the respiratory cycle information extracted by the feature extraction circuit and based on a predetermined mathematical expression, and a calibration processing circuit which calibrates a relational expression of a respiratory volume and an amplitude of a respiration curve provided in advance, based on information regarding the respiratory volume estimated by the respiratory volume estimation circuit and the amplitude information extracted by the feature extraction circuit.

A biosignal determining method according to another aspect of the present disclosure includes: obtaining information regarding cardiography representing a potential difference between two electrodes disposed on a chest of a user and detecting a peak in the cardiography; outputting an instruction to the user, the instruction including a first instruction for asking the user to perform an inhaling or exhaling motion to a limit, a second instruction for asking the user to stop the motion, and a third instruction for asking the user to perform a motion reverse to the motion to a limit; generating respiratory information regarding respiration of the user in accordance with the third instruction from a peak in the cardiography detected in a time interval starting a time when the third instruction is outputted; and determining, from a change in the respiratory information regarding the respiration of the user in accordance with the third instruction, whether the user has performed the motion asked in the first instruction to the limit.

A computer program according to still another aspect of the present disclosure to be executed by a computer provided to a biosignal determining device causes the computer to perform: obtaining information regarding cardiography representing a potential difference between two electrodes disposed on a chest of a user and detecting a peak in the cardiography; outputting an instruction to the user, the instruction including a first instruction for asking the user to perform an inhaling or exhaling motion to a limit, a second instruction for asking the user to stop the motion, and a third instruction for asking the user to perform a motion reverse to the motion to a limit; generating respiratory information regarding respiration of the user in accordance with the third instruction from a peak in the cardiography detected in a time interval starting from a time when the third instruction is outputted; and determining, from a change in the respiratory information regarding the respiration of the user in accordance with the third instruction, whether the user has performed the motion asked in the first instruction to the limit.

In the following, embodiments according to the present disclosure are described with reference to the attached drawings.

First Embodiment (Structure of Biosignal Determination System)

Figure 15:
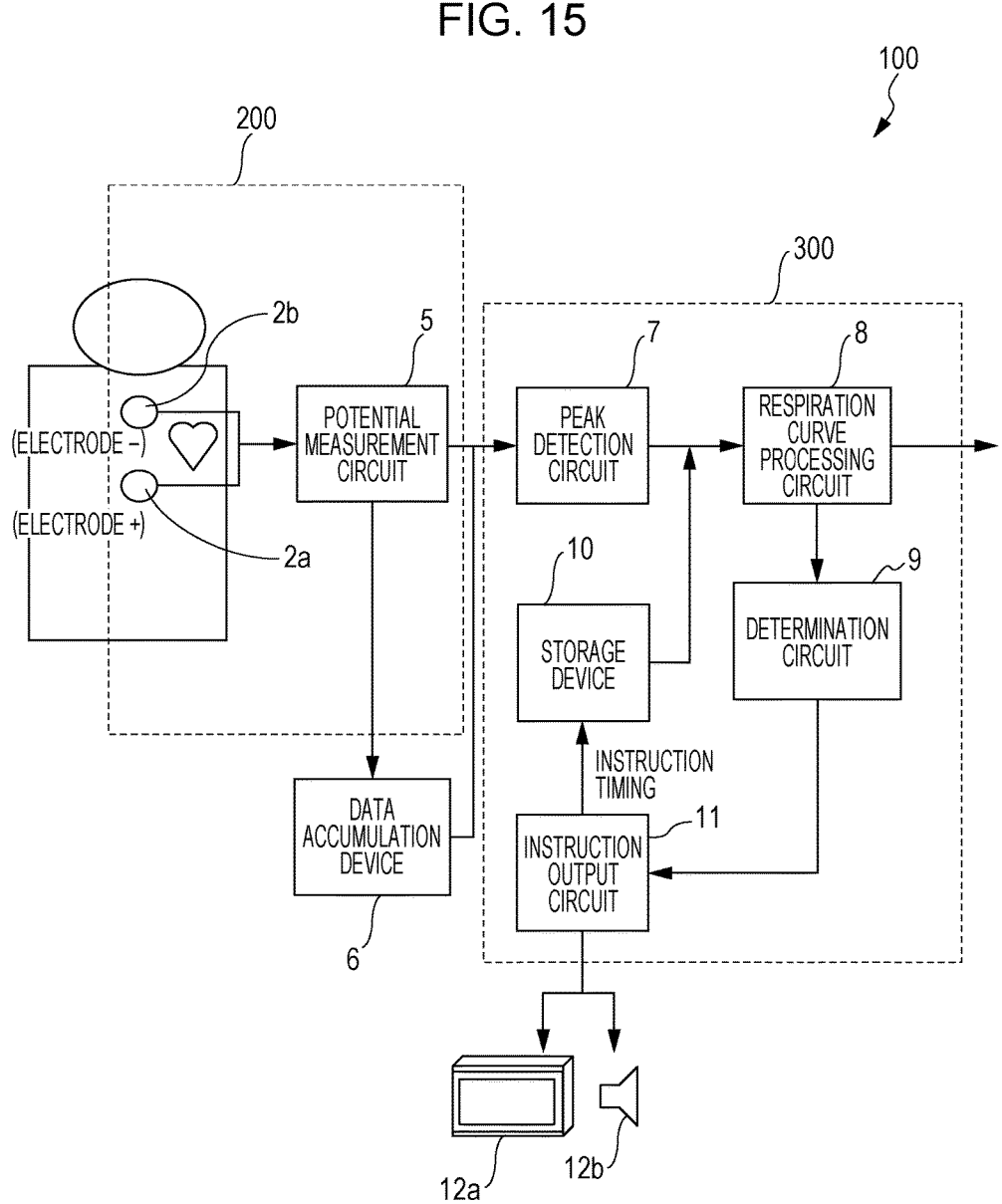
FIG. 15 is a diagram of the structure of a biosignal determination system according to a first embodiment.

FIG. 15 depicts the structure of a biosignal determination system 100 according to the present embodiment. The biosignal determination system 100 has a data accumulation device 6, a biosignal measuring device 200, and a biosignal determining device 300.

The biosignal measuring device 200 has electrodes 2a and 2b and a potential measurement circuit 5. An example of hardware of the biosignal measuring device 200 is a potential sensor including electrodes attached onto the chest of a user 1. Note that while the biosignal measuring device 200 depicted in FIG. 15 includes the electrodes 2a and 2b as components, the biosignal measuring device 200 may not include the electrodes 2a and 2b as components.

The potential measurement circuit 5 obtains information regarding potential difference by using the electrodes 2a and 2b. The information regarding potential difference corresponds to cardiographic information of the user. The electrodes 2a and 2b are disposed, for example, near a left portion of the chest of the user. Examples of the information regarding potential difference include a value indicating a potential difference between two electrodes or an impedance value.

The potential measurement circuit 5 may include a power supply electrically connected to the electrodes 2a and 2b. With a potential applied by the power supply to the electrodes 2a and 2b, an impedance value may be measured by using a potential difference between the electrodes 2a and 2b. The impedance value is obtained by dividing potentials measured by two electrodes by an applied electrical current value.

Note that the potential measurement circuit 5 may further include a ground electrode (for example, FIG. 2A to FIG. 7A). A difference between a potential difference between the electrode 2a and the ground electrode and a potential difference between the electrode 2b and the ground electrode may be found as information regarding potential difference.

The potential measurement circuit 5 obtains a potential difference or impedance value as information regarding potential difference. This information is sent to the biosignal determining device 300.

The biosignal determining device 300 has a peak detection circuit 7, a respiration curve processing circuit 8, a determination circuit 9, a storage device 10, and an instruction output circuit 11.

The peak detection circuit 7 (hereinafter referred to as "detection circuit 7") receives information regarding potential difference (cardiographic information) obtained by the biosignal measuring device 200. Based on the cardiographic information, the detection circuit 7 detects a P wave, Q wave, R wave, S wave, and T wave as peaks in cardiography. Of the P wave, Q wave, R wave, S wave, and T wave, the detection circuit 7 obtains at least the T wave. The T wave is hereinafter also represented as a "T wave peak". The P wave, Q wave, R wave, S wave, and T wave are representations each including its peak.

The detection circuit 7 may output the detected cardiographic peak in association with an instruction for the user outputted from the instruction output circuit 11.

Figure 1:
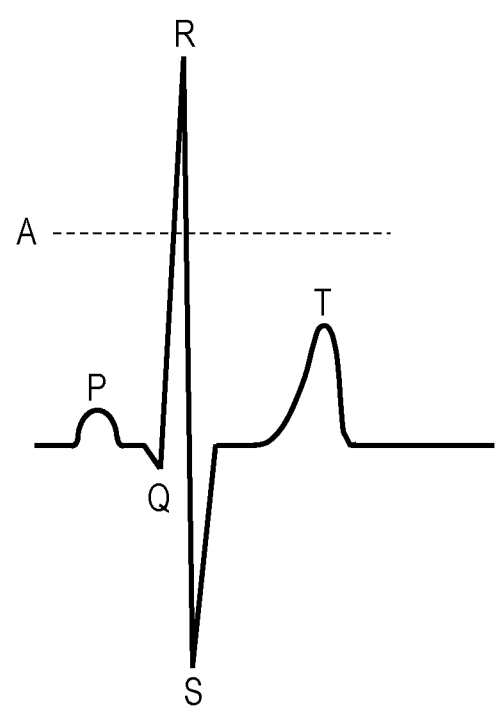
FIG. 1 is a diagram of basic components in one cycle of cardiography.
Figure 2A:
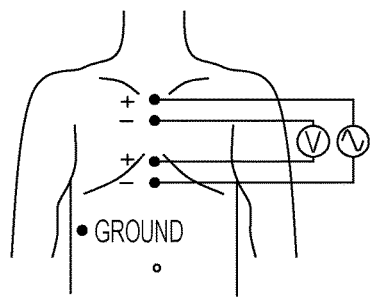
FIG. 2A is a diagram of a concept of a method described in Jeffry Bonar Fernando et. al, "Estimation of respiratory signal from thoracic impedance cardiography in low electrical current", International Conference of the IEEE Engineering in Medicine and Biology Society, pp. 3829-3832 (2013)
Figure 2B:
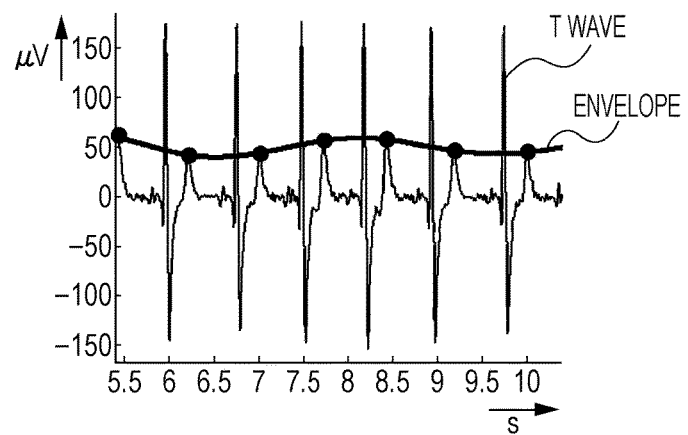
FIG. 2B is a diagram of the concept of the method described in the above cited document "Estimation of respiratory signal from thoracic impedance cardiography in low electrical current"
Figure 2C:
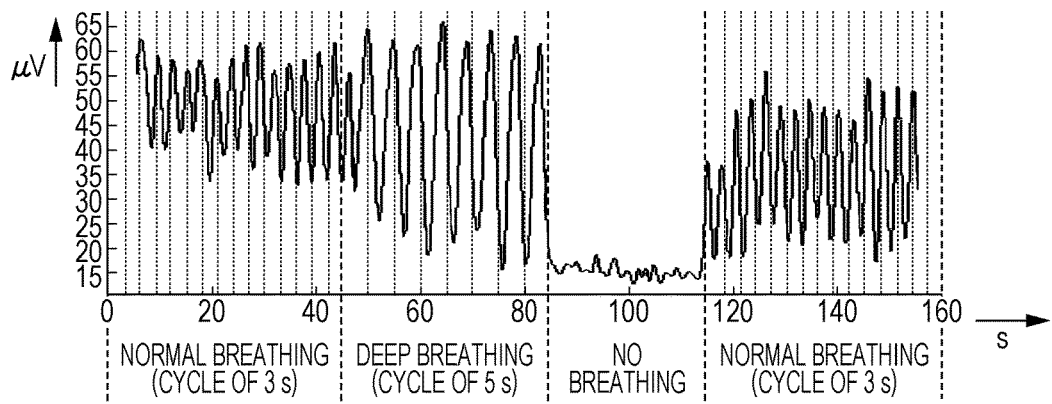
FIG. 2C is a diagram of the concept of the method described in the above cited document "Estimation of respiratory signal from thoracic impedance cardiography in low electrical current"

An example of a method of detecting a T wave peak is described below. The T wave peak can be obtained as a maximum value in the waveform example depicted in FIG. 1. In the waveform depicted in FIG. 1, for example, if the electrodes 2a and 2b are interchanged, positivity and negativity can be reversed to each other. In this case, note that the T wave peak is obtained as a minimum value.

For example, the detection circuit 7 detects an R wave in one cycle of cardiography in the information regarding potential difference obtained by the biosignal measuring device 200, and detects a maximum value after the R wave as a T wave peak. The detection circuit 7 can identify a waveform having a peak equal to or larger than a predetermined threshold (for example, a value represented by a broken line A in FIG. 1) as an R wave.

Examples of hardware of the detection circuit 7 include a potential sensor, a PC, a smartphone, and a tablet. The PC, smartphone, or tablet has a CPU which executes installed software (computer program) to receive information regarding potential difference transmitted wirelessly or by wire from the potential measurement circuit 5 and detect a T wave peak or the like by information processing based on the software.

The respiration curve processing circuit 8 (hereinafter referred to as the "processing circuit 8") extracts respiratory information regarding respiration of the user from time-series T-wave-peak information detected by the detection circuit 7. More specifically, the processing circuit 8 generates an envelope by interpolating a spline curve in each space between T wave peaks. The generated T-wave-peak envelope is used as a "respiration curve" for subsequent processing of the determination circuit 9. Note that the time-series T-wave-peak information may be information with a time when the T-wave-peak information is received by the processing circuit 8 and the T-wave-peak information associated with each other or information with each T wave peak and time associated with each other in advance. Examples of the T-wave-peak information include the potential magnitude and a waveform in a predetermined time interval.

Note that the processing circuit 8 may extract respiratory information by still another method. For example, when a T wave peak is cyclically obtained, an electrode may temporarily fall off from the user due to a movement of the user and a specific peak may disappear. In this case, the processing circuit 8 may identify a time corresponding to each T wave peak, calculate a typical value instead of a peak value by using measurement values before and after that time, and calculate a curve of respiration components from the typical value. As a typical value, for example, an average value of T wave peaks so far may be used.

Examples of hardware of the processing circuit 8 include a potential sensor, a PC, a smartphone, and a tablet. The PC, smartphone, or tablet has a CPU which executes installed software (computer program) to extract the respiratory information (envelope) by information processing based on the software.

The determination circuit 9 determines whether respiration of the user has reached its respiration limit. The "respiration limit" means an inhalation limit (full inhalation) or an exhalation limit (full exhalation).

Specifically, the determination circuit 9 specifies two timings based on an instruction timing stored in the storage device 10. The determination circuit 9 then determines whether the respiration of the user has reached the respiration limit based on a change of a respiration curve between two timings. When determining that respiration of the user has not reached the respiration limit, the determination circuit 9 again transmits an instruction to the instruction output circuit 11 to cause the instruction output circuit 11 to output an instruction for starting breathing to the user.

To determine whether the user has fully inhaled (fully exhaled), the determination circuit 9 first uses information regarding the respiration curve immediately after a timing $T_{b1}$ of an exhalation (inhalation) instruction. The determination circuit 9 determines whether the respiration curve from the timing $T_{b1}$ to a timing $(T_{b1}+\Delta T_3)$ rises or falls. It is assumed herein that the respiration curve is represented as a function Resp(t). When $\text{Resp}(T_{b1}+\Delta T_3)$ is larger than $\text{Resp}(T_{b1})$, it is determined that the respiration curve rises in that period. On the other hand, when $\text{Resp}(T_{b1}+\Delta T_3)$ is smaller than $\text{Resp}(T_{b1})$, it is determined that the respiration curve falls in that period. In the present embodiment, $\Delta T_3$ is assumed to be 1.2 s.

Based on the above-described knowledge, if the user has fully inhaled in a procedure of inhalation instruction→inhalation stop instruction→exhalation instruction, the respiration curve is supposed to fall after the exhalation instruction. That is, the respiration curve from the timing $T_{b1}$ to the timing $(T_{b1}+\Delta T_3)$ is supposed to fall. When the respiration curve rises under the above-described procedure, the determination circuit 9 can determine that the user has not fully inhaled.

Similarly, based on the above-described knowledge, if the user has fully exhaled in a procedure of exhalation instruction→exhalation stop instruction→inhalation instruction, the respiration curve is supposed to rise after the inhalation instruction. That is, the respiration curve from the timing $T_{b1}$ to the timing $(T_{b1}+\Delta T_3)$ is supposed to rise. When the respiration curve falls under the above-described procedure, the determination circuit 9 can determine that the user has not fully exhaled.

The determination circuit 9 can also determine whether respiration of the user has reached the respiration limit based on a standard deviation of the respiration curve during a stop instruction. When the standard deviation of the respiration curve in an interval from a timing $T_{s1}$ of a breathing stop instruction to the timing $T_{b1}$ of the exhalation (inhalation) instruction is equal to or larger than a predetermined threshold $\text{STD}_{th}$, the determination circuit 9 determines that the user has fully inhaled (fully exhaled). Based on the experiment results depicted in FIG. 14A and FIG. 14B, $\text{STD}_{th}$ is assumed to be 1.60 μV in the present embodiment.

Examples of hardware of the determination circuit 9 include a potential sensor, a PC, a smartphone, and a tablet. The PC, smartphone, or tablet has a CPU which executes installed software (computer program) to make a determination by information processing based on the software.

The storage device 10 has stored therein information regarding the timing $T_{s1}$ of the breathing stop instruction outputted from the instruction output circuit 11 and information regarding the timing $T_{b1}$ ($T_{s1}+\Delta T_2$) of the exhalation (inhalation) instruction outputted from the instruction output circuit 11. The storage device 10 is, for example, a semiconductor memory. Note that the storage device 10 may be provided as a storage element such as a register or buffer provided in the instruction output circuit 11.

At any timing or in response to an instruction from the determination circuit 9, the instruction output circuit 11 outputs an instruction for starting or stopping breathing to the user. Breathing includes inhalation and exhalation. The instruction includes a first instruction for asking the user to perform an inhaling or exhaling motion to the limit, a second instruction for asking the user to stop the motion, and a third instruction for asking the user to perform a motion reverse to the above-described motion.

This instruction is outputted as an audio signal and/or picture signal. The picture signal is sent to a display device 12a and is presented by the display device 12a as picture on its display surface. The picture is, for example, a still image, a moving image, and/or text. The audio signal is sent to a loudspeaker 12b and is presented by the loudspeaker 12b as audio. With this, the instruction to the user is achieved by presenting audio and/or a message on the display surface. For example, for starting inhalation and exhalation, the instruction output circuit 11 presents instructions "inhale" and "exhale" by audio and/or characters. Alternatively, for stopping breathing, the instruction output circuit 11 presents an instruction "stop breathing" by audio and/or characters.

Note that presentation of audio and/or presentation on the display is merely an example. As another example, the instruction output circuit 11 may make each of the instructions for inhalation, exhalation, and stopping breathing by lighting up and lighting out. In this case, the instruction output circuit 11 generates a signal for lighting up and lighting out and outputs the signal as an instruction.

Note that an expression "the instruction output circuit 11 instructs the user" used in the specification means that audio and/or picture such as characters is presented to ask the user to inhale, exhale, or stop breathing.

Also, the instruction output circuit 11 asks the user to stop breathing after a predetermined time $\Delta T_1$ has passed. For example, for stopping breathing, the instruction output circuit 11 presents an instruction "stop breathing after $\Delta T_1$ seconds" by audio and/or characters.

In the present embodiment, for example, $\Delta T_1$ is set initially at four seconds (s). Note that $\Delta T_1$ may not be fixed and may be variable. In the determination circuit 9 described further below, when it is determined that the user has not fully inhaled (fully exhaled) and a breathing start instruction is again provided from the start, the instruction output circuit 11 may set a longer value as $\Delta T_1$.

A period of a breathing stop instruction is a period $\Delta T_2$. When an instruction for the user to inhale is provided before a stop instruction, the instruction output circuit 11 outputs an instruction to prompt the user to exhale after $\Delta T_2$. On the other hand, when an instruction for the user to exhale is provided before a stop instruction, the instruction output circuit 11 outputs an instruction to prompt the user to inhale after $\Delta T_2$. Note that to clarify a difference in fluctuations between full inhalation (full exhalation) and otherwise, $\Delta T_2$ is assumed to be equal to or larger than 4 s, based on the experiment results depicted in FIG. 12A, FIG. 12B, FIG. 13A, and FIG. 13B.

The instruction output circuit 11 can be achieved as an audio processing circuit which generates an audio signal as described above and/or an image processing circuit which generates a character signal as described above. However, a general-purpose processor such as a CPU can operate as the instruction output circuit 11. Therefore, the instruction output circuit 11 may be a CPU of a PC, a smartphone, or a tablet. By executing installed software (computer program), the CPU can generate an audio signal and/or picture signal for presenting an instruction to the user by information processing based on the software.

The data accumulation device 6 is, for example, a recording medium itself and/or a recording device including a recording medium, and accumulates potential differences or impedance values transmitted from the potential measurement circuit 5. The recording medium can be a semiconductor recording medium, a magnetic recording medium, an optical recording medium, or the like. Note that the data accumulation device 6 may not be provided. For example, if potential differences and impedance values can be retained in a register of the CPU, that register can be used in place of the data accumulation device 6.

(Entire Process Flow)

Figure 16:
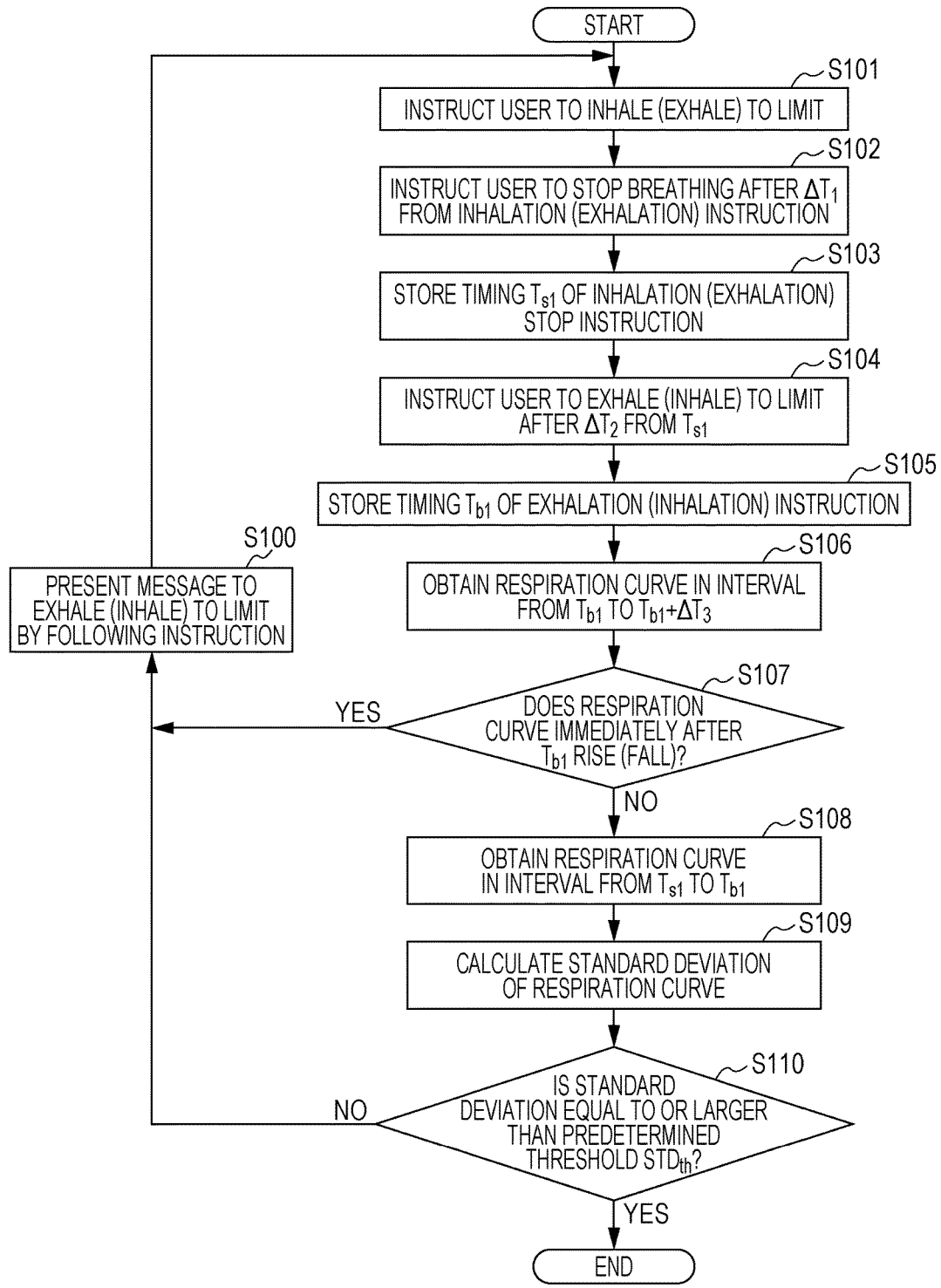
FIG. 16 is a flowchart of the procedure of a process of the biosignal determination system according to the first embodiment.

FIG. 16 depicts the procedure of a process of the biosignal determination system 100 of the present embodiment. Note that in each of "inhale/inhalation (exhale/exhalation)", "exhale/exhalation (inhale/inhalation)", and "rise (fall)" in description of the steps S101 to S105, and S107 described further below, the former or latter (in parentheses) is uniformly selected for all steps. For example, when "inhale" is selected from "inhale (exhale)" at step S101, the former motion in the description is selected in each of the following steps. That is, "inhalation" is selected at steps S102 and S103, "exhale/exhalation" is selected at steps S104 and S105, and "rise" is selected at step S107. The opposite applies when "exhale" is selected from "inhale (exhale)" at step S101.

<Step S101>

The instruction output circuit 11 instructs the user to inhale (exhale) to the limit. The instruction herein is also represented as a "first instruction".

<Step S102>

The instruction output circuit 11 further instructs the user to stop breathing after $\Delta T_1$ from the breathing start instruction outputted at step S101. The instruction herein subsequent to the first instruction is also represented as a "second instruction".

<Step S103>

The storage device 10 stores information regarding the timing $T_{s1}$ of the breathing stop instruction issued at step S102.

<Step S104>

The instruction output circuit 11 instructs the user to exhale (inhale) after $\Delta T_2$ from the timing $T_{s1}$ of the breathing stop instruction issued at step S102. The instruction herein subsequent to the second instruction is also represented as a "third instruction".

<Step S105>

The storage device 10 stores information regarding the timing $T_{b1}$ of the exhalation (inhalation) instruction issued at step S104.

<Step S106>

The processing circuit 8 obtains a respiration curve including an interval from the timing $T_{b1}$ of the exhalation (inhalation) instruction stored at step S105 to $(T_{b1}+\Delta T_3)$. Here, the interval from the timing $T_{b1}$ to $(T_{b1}+\Delta T_3)$ is also represented as a time interval starting from the time when the third instruction is outputted.

<Step S107>

The determination circuit 9 determines whether the user has inhaled (exhaled) to the limit, that is, the user has fully inhaled (fully exhaled), by using the respiration curve obtained at step S106. Specifically, the determination circuit 9 determines whether the respiration curve between two timings, that is, from $T_{b1}$ to $(T_{b1}+\Delta T_3)$, rises or falls. For example, the determination circuit 9 determines the respiration curve by using the inclination of the respiration curve or the potential magnitude.

For example, the determination circuit 9 determines a respiration curve with a positive inclination at a time immediately after the timing $T_{b1}$ as rising. Also, the determination circuit 9 determines a respiration curve with a negative inclination at a time immediately after the timing $T_{b1}$ as falling.

Furthermore, the determination circuit 9 determines a respiration curve with a minimum value of the timing $T_{b1}$ as rising. Still further, the determination circuit 9 determines a respiration curve with a maximum value of the timing $T_{b1}$ as falling. Still further, a respiration curve with a value equal to or larger than the threshold after a predetermined time from the timing $T_{b1}$ is determined as rising. Still further, a respiration curve with a value smaller than the threshold after a predetermined time from the timing $T_{b1}$ is determined as falling.

When an inhalation instruction is provided at step S101, an inhalation stop instruction is provided at step S102, and then an exhalation instruction is provided at step S104, if the respiration curve from $T_{b1}$ to $(T_{b1}+\Delta T_3)$ rises, it is determined that the user has not fully inhaled. Similarly, when an exhalation instruction is provided at step S101, an exhalation stop instruction is provided at step S102, and then an inhalation instruction is provided at step S104, if the respiration curve from $T_{b1}$ to $(T_{b1}+\Delta T_3)$ falls, it is determined that the user has not fully exhaled. If it is determined that the user has not fully inhaled (has not fully exhaled), the process proceeds to step S100. Otherwise, the process proceeds to step S108.

<Step S108>

The processing circuit 8 obtains a respiration curve in an interval from the timing $T_{s1}$ of the breathing stop instruction stored at step S103 to the timing $T_{b1}$ of the exhalation (inhalation) instruction stored at step S105.

<Step S109>

The determination circuit 9 calculates a standard deviation of the respiration curve obtained at step S108.

<Step S110>

The determination circuit 9 determines whether the user has inhaled (exhaled) to the limit, that is, the user has fully inhaled (fully exhaled), by using the standard deviation calculated at step S109. Specifically, when the standard deviation is equal to or larger than the predetermined threshold $STD_{th}$, it is determined that the user has fully inhaled (fully exhaled), and then ends the entire process flow. Otherwise, the process proceeds to step S100.

<Step S100>

The instruction output circuit 11 generates an audio signal and/or a picture signal to present a message by audio and/or picture to the user to exhale (inhale) to the limit by following an instruction.

In the foregoing, regarding the biosignal determination system 100 according to the present embodiment, a main structure and operation of the biosignal determining device 300 are mainly described. Regarding the above-described step S110, while a process after it is determined that the user has exhaled (inhaled) to the limit by following the instruction and the process of FIG. 16 ends has not been mentioned, the following process may be additionally performed, for example.

That is, from the time-series T-wave-peak information obtained so far, the processing circuit 8 generates an envelope (respiration curve) by interpolating a spline curve between T wave peaks. The processing circuit 8 may output information regarding a respiratory rate by counting the number of peaks in the respiration curve as the respiratory rate of the user. In consideration of performing operation as described above, the biosignal determination system 100 and the biosignal determining device 300 can be referred to as a biosignal measurement system and biosignal measuring device including a calibration function.

Second Embodiment (Structure of Biosignal Determination System)

Figure 17:
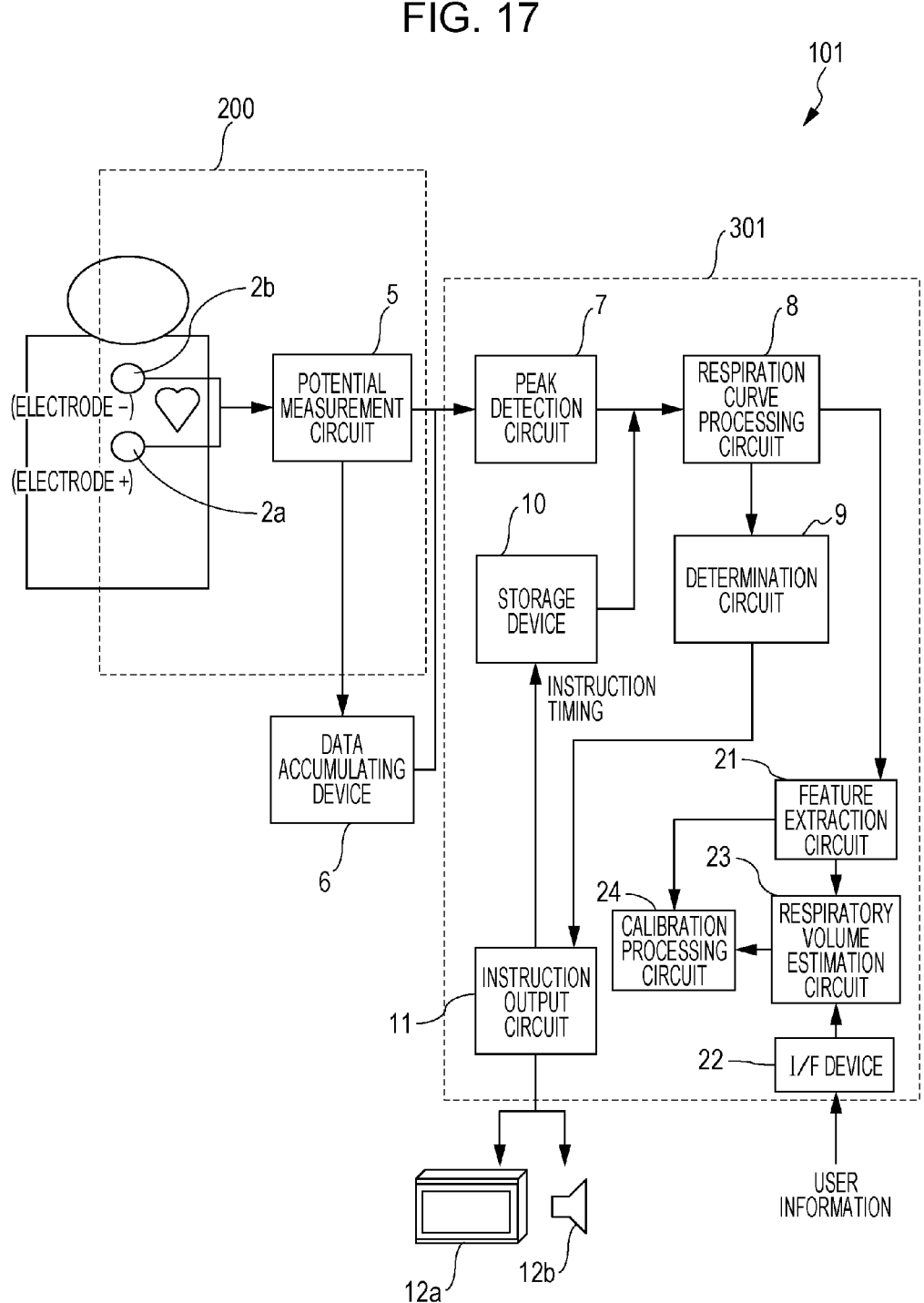
FIG. 17 is a diagram of the structure of a biosignal determination system according to a second embodiment.

FIG. 17 depicts the structure of a biosignal determination system 101 according to the present embodiment. The biosignal determination system 101 has the data accumulation device 6, the biosignal measuring device 200, and a biosignal determining device 301.

The biosignal determining device 301 according to the present embodiment is configured by further adding, to the biosignal determining device 300 of the first embodiment, a feature extraction circuit 21, an interface (I/F) device 22, a respiratory volume estimation circuit 23, and a calibration processing circuit 24.

The biosignal measuring device 200 and the processing circuit 8, the determination circuit 9, the storage device 10, and the instruction output circuit 11 in the biosignal determining device 301 are provided with the same reference numerals as those in FIG. 15 and are not described herein.

In the following, the feature extraction circuit 21, the I/F device 22, the respiratory volume estimation circuit 23, and the calibration processing circuit 24 are described.

The feature extraction circuit 21 mainly extracts two pieces of information from the respiration curve obtained by the processing circuit 8 in the specified time interval. Specifically, these two pieces of information are respiratory cycle information and amplitude information, which are specifically described below.

The feature extraction circuit 21 extracts the respiratory cycle information and the amplitude information from the respiration curve obtained by the processing circuit 8 in the specified time interval. In this time interval, a maximum value and a minimum value of the respiration curve are assumed to be $\text{Resp}_{max}$ and $\text{Resp}_{min}$. When it is assumed that times corresponding thereto are $t(\text{Resp}_{max})$ and $t(\text{Resp}_{min})$, respectively, a respiratory cycle T can be found from the following Equation 6. Also, an amplitude Amp can be found from the following Equation 7.

$$T = 2 \times |t(\text{Resp}_{max}) - t(\text{Resp}_{min})| \quad \text{(Equation 6)}$$

$$\text{Amp} = \text{Resp}_{max} - \text{Resp}_{min} \quad \text{(Equation 7)}$$

The feature extraction circuit 21 may be a CPU of a PC, a smartphone, or a tablet. By executing installed software (computer program), the CPU can extract the respiratory cycle T and the amplitude Amp described above from Equation 6 and Equation 7 mentioned above, by information processing based on the software.

The I/F device 22 obtains information regarding gender, age, and height of the user. These pieces of information are inputted by the user in advance.

The I/F device 22 may be an input device such as a touch screen, a keyboard, or a mouse, or may be a terminal provided to the biosignal determining device 301 for connecting an external device. The latter example may be an Ethernet® terminal for connecting the biosignal determining device 301 to a network. When the input device such as a keyboard or mouse is not a component of the biosignal determining device 301, the I/F device 22 can be, for example, a USB terminal or a PS/2 terminal.

The respiratory volume estimation circuit 23 estimates a respiratory volume of the user. A maximum respiratory volume of the user is estimated from Equation 3 mentioned above by using the gender, age, and height of the user obtained by the I/F device 22. A respiratory volume in a second instruction onward is estimated from Equation 5 mentioned above by using the respiratory cycle obtained by the feature extraction circuit 21.

The respiratory volume estimation circuit 23 may be a CPU of a PC, a smartphone, or a tablet. By executing installed software (computer program), the CPU can estimate a respiratory volume from Equation 5 mentioned above, by information processing based on the software.

The calibration processing circuit 24 calibrates a relational expression of the respiratory volume and the amplitude from the amplitude obtained by the feature extraction circuit 21 and the respiratory volume estimated by the respiratory volume estimation circuit 23. Specifically, two amplitudes $\text{Amp}_1$ and $\text{Amp}_2$ obtained by the feature extraction circuit 21 and two respiratory volumes $V_1$ and $V_2$ estimated by the respiratory volume estimation circuit 23 are approximated by a quadric curve. From coordinates of three points $(0, 0)$, $(\text{Amp}_1, V_1)$, and $(\text{Amp}_2, V_2)$, a quadric curve approximate expression is found, and this approximate expression is taken as a relational expression of the respiratory volume and the amplitude.

Note that when the number of amplitudes obtained by the feature extraction circuit 21 and the number of respiratory volumes estimated by the respiratory volume estimation circuit 23 are each three or more, a polynomial expression may be used for approximation.

The calibration processing circuit 24 may also be a CPU of a PC, a smartphone, or a tablet. By executing installed software (computer program), the CPU can perform a calibration process described further below, by information processing based on the software.

The process of the biosignal determining device 301 is described in detail below.

(Entire Process Flow)

Figure 18:
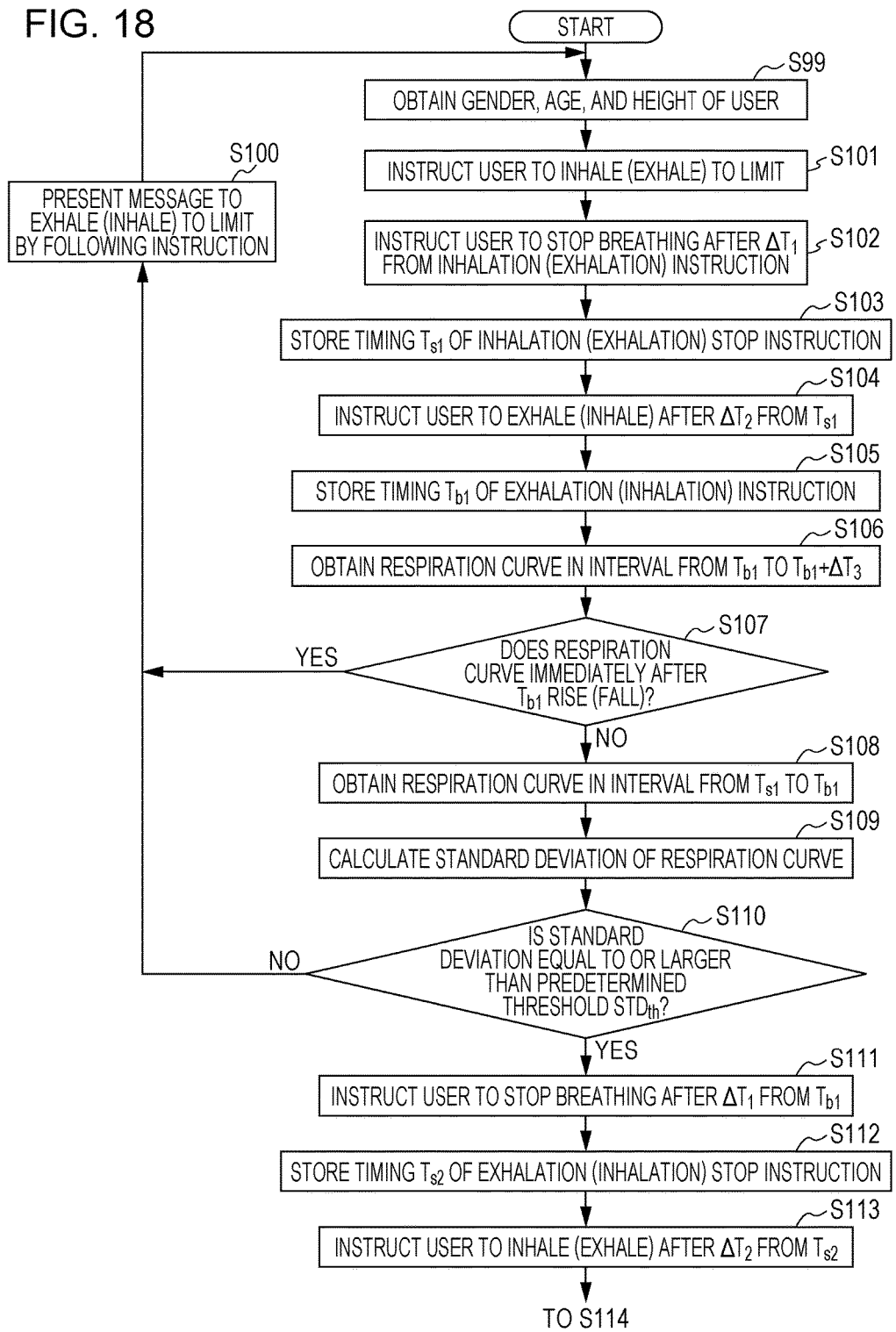
FIG. 18 is a flowchart of the procedure of a process of the biosignal determination system of the second embodiment.
Figure 19:
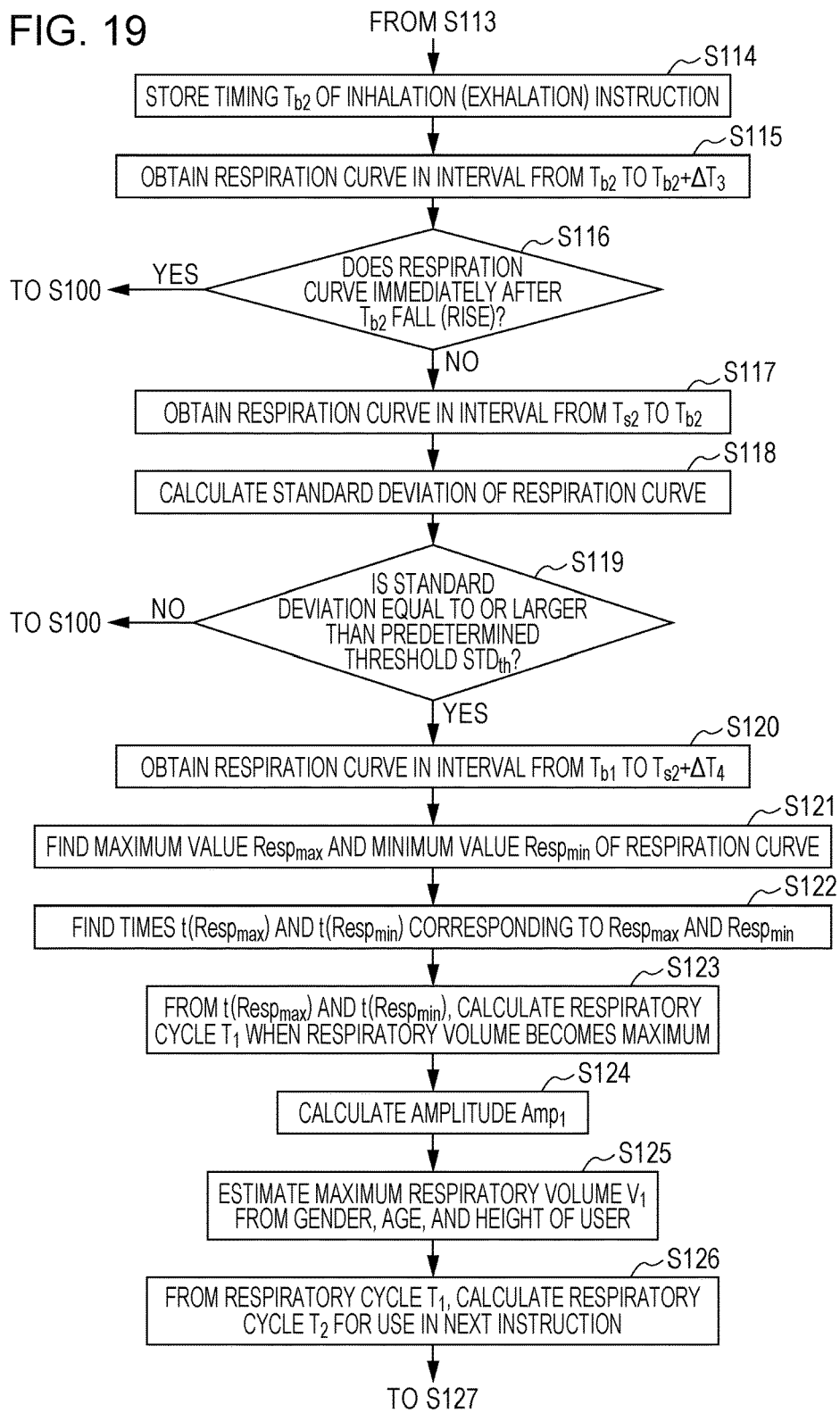
FIG. 19 is a flowchart of the procedure of the process of the biosignal determination system of the second embodiment (continued from FIG. 18)
Figure 20:
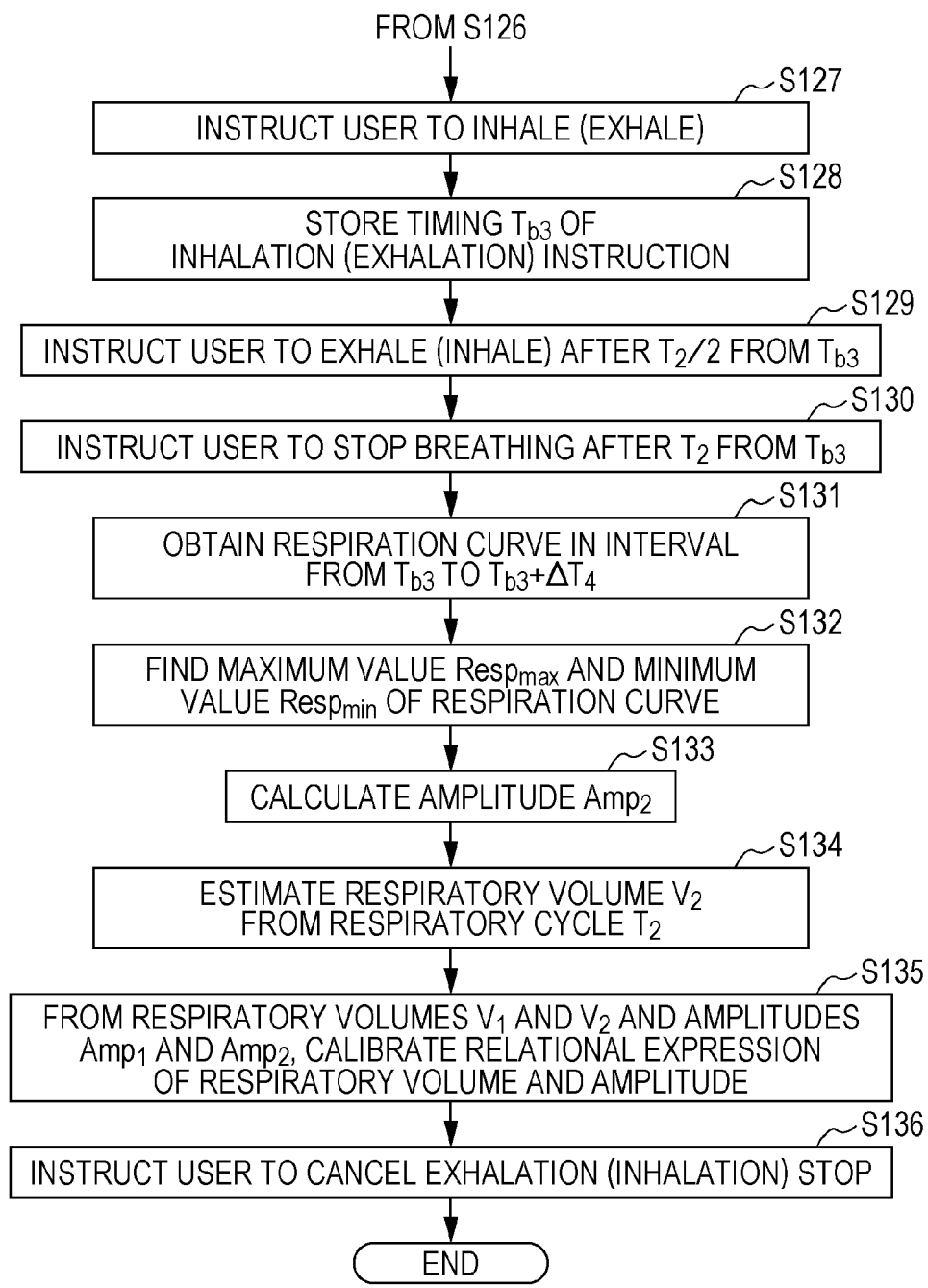
FIG. 20 is a flowchart of the procedure of the process of the biosignal determination system of the second embodiment (continued from FIG. 19)

FIG. 18 to FIG. 20 depict the procedure of a process of the biosignal determination system 101 of the present embodiment. Since the procedure is long, the procedure is depicted as being divided into three drawings.

<Step S99>

From the user, the I/F device 22 obtains the information regarding gender, age, and height of the user.

<Steps S100 to S110>

Processes at steps S100 to S110 are similar to the processes of the first embodiment (FIG. 16), and therefore are not described in the present embodiment.

<Step S111>

The instruction output circuit 11 instructs the user to stop breathing after $\Delta T_1$ from the timing $T_{b1}$ of the exhalation (inhalation) instruction stored at step S105.

<Step S112>

The storage device 10 stores a timing $T_{s2}$ of the breathing stop instruction issued at step S111.

<Step S113>

The instruction output circuit 11 instructs the user to inhale (exhale) after $\Delta T_2$ from the timing $T_{s2}$ of the breathing stop instruction issued at step S112.

<Step S114>

The storage device 10 stores a timing $T_{b2}$ of the inhalation (exhalation) instruction issued at step S113.

<Step S115>

The processing circuit 8 obtains a respiration curve in an interval from the timing $T_{b2}$ of the inhalation (exhalation) instruction stored at step S114 to $T_{b2} + \Delta T_3$.

<Step S116>

By using the respiration curve obtained at step S115, the determination circuit 9 determines whether the user has exhaled (inhaled) to the limit. That is, the determination circuit 9 determines whether the user has fully exhaled (fully inhaled). Specifically, the determination circuit 9 determines whether the respiration curve from $T_{b2}$ to $(T_{b2}+\Delta T_3)$ rises or falls. When an exhalation instruction is presented at step S104, an exhalation stop instruction is presented at step S111, and an inhalation instruction is presented at step S113, the determination circuit 9 determines that the user has not fully exhaled if the respiration curve from $T_{b2}$ to $(T_{b2}+\Delta T_3)$ falls. Similarly, when an inhalation instruction is presented at step S104, an inhalation stop instruction is presented at step S111, and an exhalation instruction is presented at step S113, the determination circuit 9 determines that the user has not fully inhaled if the respiration curve from $T_{b2}$ to $(T_{b2}+\Delta T_3)$ rises. If determining that the user has not fully exhaled (fully inhaled), the determination circuit 9 returns to the process at step S100. Otherwise, the process proceeds to step S117.

<Step S117>

The processing circuit 8 obtains a respiration curve in an interval from the timing $T_{s2}$ of the breathing stop instruction stored at step S112 to the timing $T_{b2}$ of the inhalation (exhalation) instruction stored at step S114.

<Step S118>

The determination circuit 9 calculates a standard deviation of the respiration curve obtained at step S117.

<Step S119>

By using the standard deviation calculated at step S118, the determination circuit 9 determines whether exhalation (inhalation) of the user has reached its limit. That is, the determination circuit 9 determines whether the user has fully exhaled (fully inhaled). Specifically, when the standard deviation is equal to or larger than the predetermined threshold $STD_{th}$, the determination circuit 9 determines that the user has fully exhaled (fully inhaled), and then proceeds to step S120. Otherwise, the determination circuit 9 returns to the process at step S100.

<Step S120>

The processing circuit 8 obtains a respiration curve from the timing $T_{b1}$ of the exhalation (inhalation) instruction stored at step S105 after $\Delta T_4$ from the timing $T_{s2}$ of the exhalation (inhalation) stop instruction stored at step S112 $(T_{s2}+\Delta T_4)$. $\Delta T_4$ is a time for consideration of a delay from the instruction until the user actually makes a motion. In the present embodiment, $\Delta T_4$ is assumed to be 1 s.

<Step S121>

From the respiration curve obtained at step S120, the processing circuit 8 finds a maximum value $Resp_{max}$ and a minimum value $Resp_{min}$ of the respiration curve.

<Step S122>

The processing circuit 8 finds times $t(Resp_{max})$ and $t(Resp_{min})$ corresponding to the maximum value $Resp_{max}$ and the minimum value $Resp_{min}$, respectively, found at step S121.

<Step S123>

From the times $t(Resp_{max})$ and $t(Resp_{min})$ found at step S122, the feature extraction circuit 21 calculates a respiratory cycle $T_1$ when the respiratory volume becomes maximum. The respiratory cycle $T_1$ is calculated by using Equation 6 mentioned above.

<Step S124>

The feature extraction circuit 21 calculates an amplitude $Amp_1$ from the maximum value $Resp_{max}$ and the minimum value $Resp_{min}$ found at step S121. The amplitude $Amp_1$ is calculated by using Equation 7 mentioned above.

<Step S125>

From the information regarding gender, age, and height of the user obtained at step S99, the respiratory volume estimation circuit 23 estimates a maximum respiratory volume $V_1$ by using Equation 3 mentioned above.

<Step S126>

From the respiratory cycle $T_1$ calculated at step S123, the feature extraction circuit 21 calculates a respiratory cycle $T_2$ for use in the next instruction by using, for example, Equation 4 mentioned above.

<Step S127>

The instruction output circuit 11 instructs the user to start inhalation (exhalation).

<Step S128>

The storage device 10 stores a timing $T_{b3}$ of the inhalation (exhalation) instruction issued at step S127.

<Step S129>

The instruction output circuit 11 instructs the user to start exhalation (inhalation) after $T_2/2$ from $T_{b3}$ by using the timing $T_{b3}$ of the inhalation (exhalation) instruction stored at step S128 and the respiratory cycle $T_2$ calculated at step S126.

<Step S130>

The instruction output circuit 11 instructs the user to stop breathing after $T_2$ from $T_{b3}$ by using the timing $T_{b3}$ of the inhalation (exhalation) instruction stored at step S128 and the respiratory cycle $T_2$ calculated at step S126.

<Step S131>

The processing circuit 8 obtains a respiration curve in an interval from the timing $T_{b3}$ of the inhalation (exhalation) instruction stored at step S128 to $(T_{b3}+\Delta T_4)$.

<Step S132>

From the respiration curve obtained at step S131, the processing circuit 8 finds a maximum value $Resp_{max}$ and a minimum value $Resp_{min}$ of the respiration curve.

<Step S133>

The feature extraction circuit 21 calculates an amplitude $Amp_2$ from the maximum value $Resp_{max}$ and the minimum value $Resp_{min}$ found at step S132. The amplitude $Amp_2$ is calculated by using Equation 7 mentioned above.

<Step S134>

From the respiratory cycle $T_2$ calculated at step S126 and the respiratory volume $V_1$ estimated at step S125, the respiratory volume estimation circuit 23 estimates a respiratory volume $V_2$. The respiratory volume $V_2$ is calculated by using Equation 5 mentioned above.

<Step S135>

The calibration processing circuit 24 calibrates a relational expression of the respiratory volume and the amplitude from the respiratory volume $V_1$ estimated at step S125, the respiratory volume $V_2$ estimated at step S134, the amplitude $Amp_1$ obtained at step S124, and the amplitude $Amp_2$ obtained at step S133. Specifically, two amplitudes $Amp_1$ and $Amp_2$ obtained by the feature extraction circuit 21 and two respiratory volumes $V_1$ and $V_2$ estimated by the respiratory volume estimation circuit 23 are approximated by a quadric curve. From coordinates of three points $(0, 0)$, $(Amp_1, V_1)$, and $(Amp_2, V_2)$, a quadric curve approximate expression is found, and this approximate expression is taken as a relational expression of the respiratory volume and the amplitude.

<Step S136>

The instruction output circuit 11 instructs the user to cancel exhalation (inhalation) stop.

Note that the processes at steps S126 to S134 may be again performed after step S134. The processes in repetition are referred to be step S126a, step S127a, step S128a, step S129a, step S130a, step S131a, step S132a, step S133a, and step S134a. In this case, $T_2$ at step S126 is replaced by $T_3$ at step S126a. $T_3$ is assumed to be $T_1/3$, for example. The processes at steps S127a to S134a are performed on $T_3$. Thus, $Amp_3$ is calculated at step S133a, and $V_3$ is estimated at step S135a. The processes at steps S126 to S134 may be performed several times. After the end of a predetermined number of repetitions, the process proceeds to step S135. In this case, since the number of amplitudes obtained by the feature extraction circuit 21 and the number of respiratory volumes estimated by the respiratory volume estimation circuit 23 are each three or more, a polynomial expression may be used to approximate a relational expression of the respiratory volume and the amplitude.

The structure and operation according to the present embodiment have been described above.

In each of the embodiments described above, the operation of the biosignal determining device has been described by using the respiration curve found as an envelope of T wave peaks in cardiography. However, this is merely an example. While the respiration curve is an envelope and continuous, the processes described above can be achieved by using a discrete potential difference or impedance value.

Third Embodiment

Figure 29:
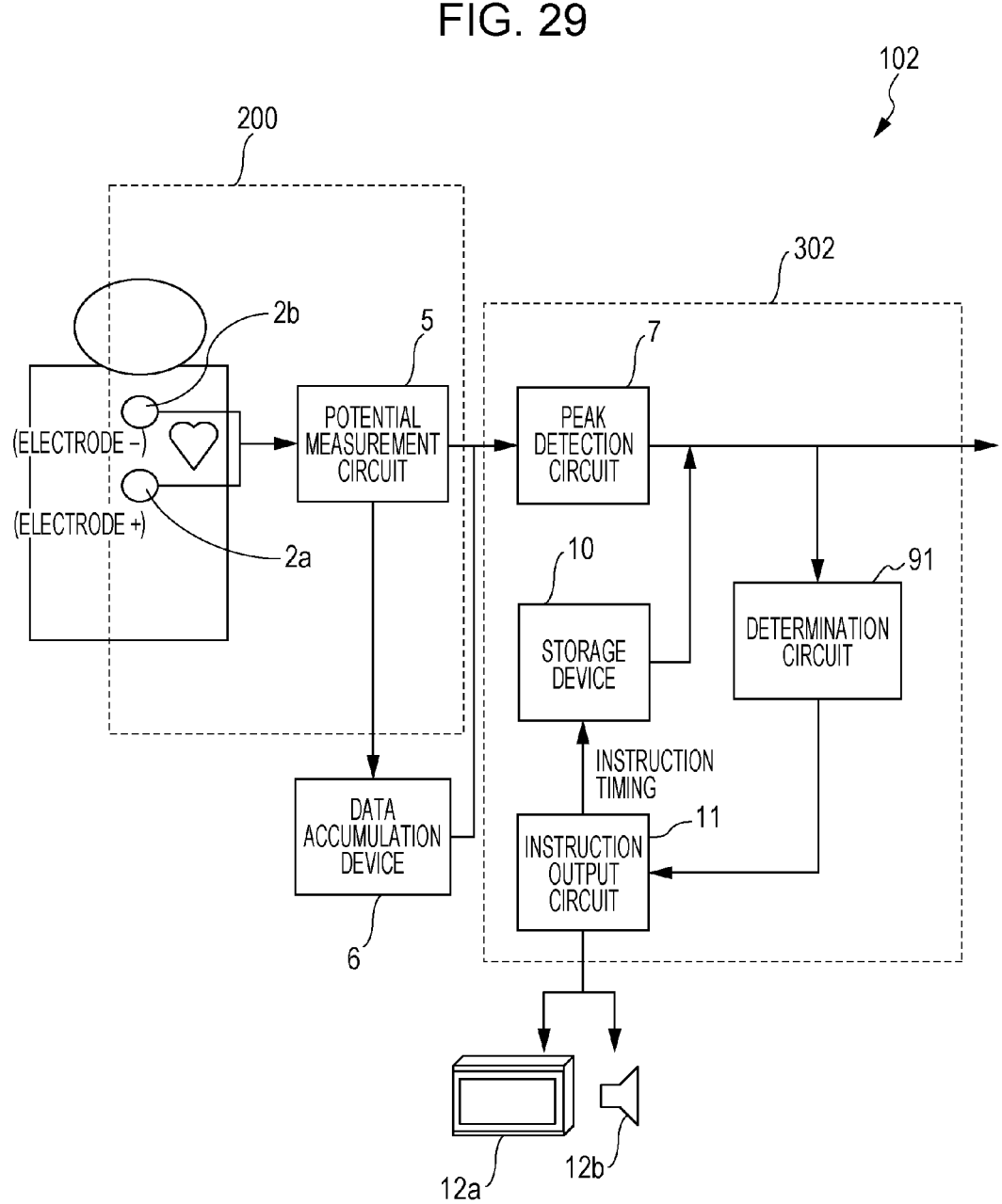
FIG. 29 is a diagram of the structure of a biosignal determination system according to a third embodiment.

FIG. 29 depicts the structure of a biosignal determination system 102 according to the present embodiment. The biosignal determination system 102 includes the data accumulation device 6, the biosignal measuring device 200, and a biosignal determining device 302.

Unlike the biosignal determination system 100 according to the first embodiment, the biosignal determination system 102 according to the third embodiment does not have the respiration curve processing circuit 8. The biosignal determination system 102 according to the third embodiment can determine whether the user has fully inhaled or fully exhaled by using a discrete potential difference or impedance value.
(Determination Circuit 91)

Based on a potential value at the peak in cardiography detected by the detection circuit 7, a determination circuit 91 determines whether respiration of the user has reached the respiration limit.
(Entire Process Flow)

Figure 30:
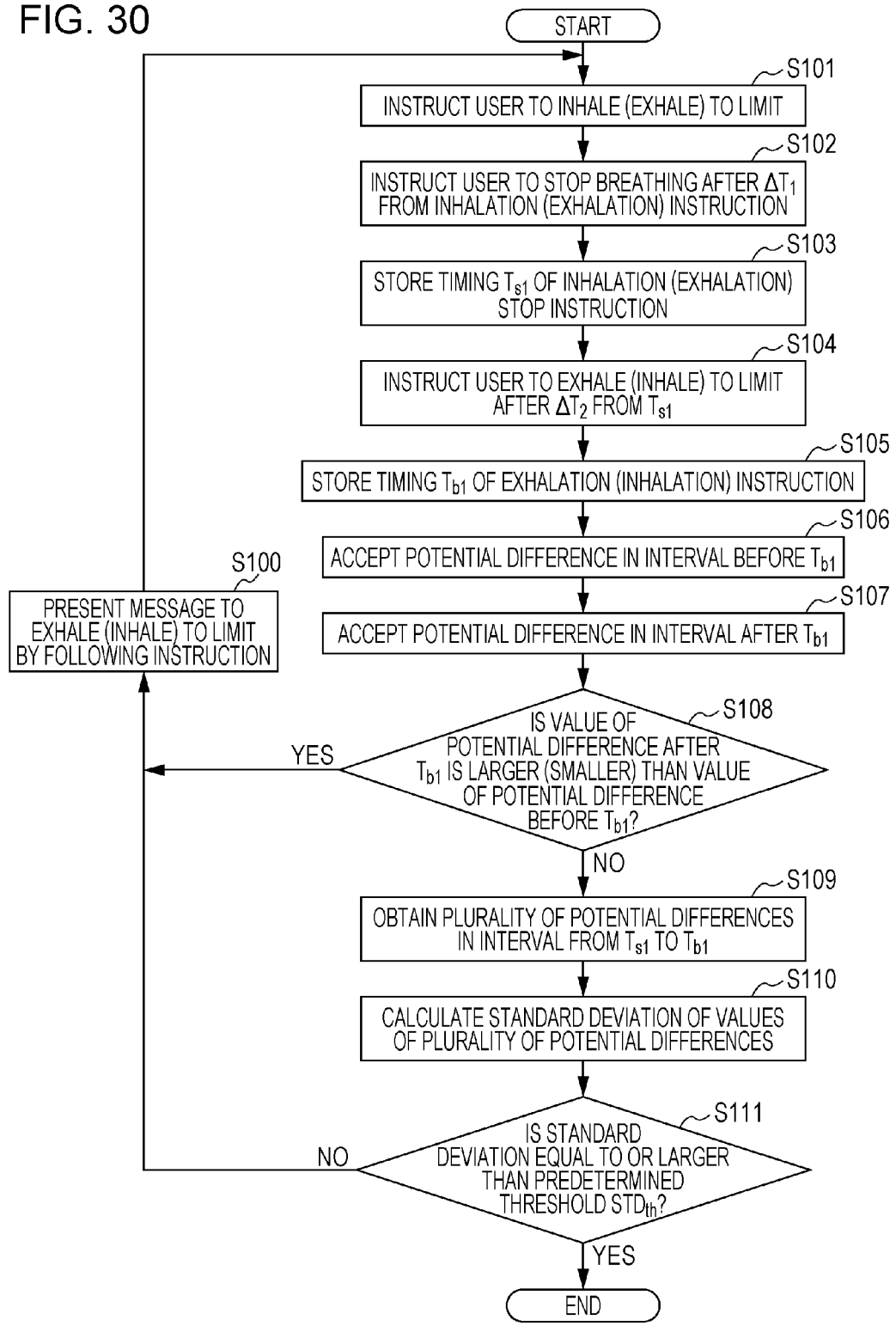
FIG. 30 is a flowchart of the procedure of a process of the biosignal determination system according to the third embodiment.

FIG. 30 depicts the procedure of a process of the biosignal determination system 102 of the present embodiment. Since steps S101 to S105 are identical to those of the first embodiment, these steps are not described herein.
<Step S106>

The determination circuit 91 refers to the timings $T_{s1}$ and $T_{b1}$ of the exhalation (inhalation) instructions stored at steps S103 and S105, respectively, and obtains information regarding a potential difference (cardiographic information) including an interval from $T_{s1}$ to $T_{b1}$ from the peak detection circuit 7.
<Step S107>

The determination circuit 91 refers to the timing $T_{b1}$ of the exhalation (inhalation) instruction stored at step S105, and obtains the information regarding a potential difference (cardiographic information) including an interval from $T_{b1}$ to $T_{b1}+\Delta T_4$. Here, $\Delta T_4$ is a predetermined time including at least one T wave peak. $\Delta T_4$ is desirably a time including two T wave peaks, that is, a second T wave peak after $T_{b1}$.
<Step S108>

By using the value of the potential difference obtained at step S106 and the value of the potential difference obtained at step S107, the determination circuit 91 determines whether the user has inhaled (exhaled) to the limit, that is, whether the user has fully inhaled (fully exhaled). Specifically, the determination circuit 91 determines whether the value of the potential difference obtained at step S107 is larger or smaller than the value of the potential difference obtained at step S106.

When a plurality of potential difference values are obtained at step S107, it is determined whether the plurality of obtained potential differences are larger than the value of the potential difference obtained at step S106.

When an inhalation instruction is provided at step S101, an inhalation stop instruction is provided at step S102, and an exhalation instruction is provided at step S104, if the value of the potential difference obtained at step S107 is larger than the value of the potential difference obtained at step S106, it is determined that the user has not fully inhaled. Similarly, when an exhalation instruction is provided at step S101, an exhalation stop instruction is provided at step S102, and an inhalation instruction is provided at step S104, if the value of the potential difference obtained at step S107 is smaller than the value of the potential difference obtained at step S106, it is determined that the user has not fully exhaled. If it is determined that the user has not fully inhaled (not fully exhaled), the process proceeds to step S100. Otherwise, the process proceeds to step S109.
<Step S109>

The determination circuit 91 refers to the timings $T_{s1}$ and $T_{b1}$ of the exhalation (inhalation) instructions stored at steps S103 and S105, and obtains information regarding all potential differences in an interval from $T_{s1}$ to $T_{b1}$ (cardiographic information) from the peak detection circuit 7. Here, the information regarding all potential differences are a plurality of peaks in cardiography included in the interval from $T_{s1}$ to $T_{b1}$.
<Step S110>

The determination circuit 91 calculates a standard deviation of the information regarding all potential differences obtained at step S109.
<Step S111>

By using the standard deviation calculated at step S110, the determination circuit 91 determines whether the user has inhaled (exhaled) to the limit, that is, whether the user has fully inhaled (fully exhaled). Specifically, when the standard deviation is equal to or larger than the predetermined threshold $STD_{th}$, it is determined that the user has fully inhaled (fully exhaled), and ends the entire process flow. Otherwise, the process proceeds to step S100.
<Step S100>

The instruction output circuit 11 generates an audio signal and/or picture signal and presents a message by audio and/or picture for the user to exhale (inhale) to the limit by following an instruction.

Note that while the determination circuit 91 makes a determination by using the standard deviation at steps S110 and S111, it may be determined whether the user has inhaled (exhaled) to the limit depending on whether all potential differences are included in a predetermined numerical value range.
(First Modification Example of Third Embodiment)

A biosignal determination system 103 according a first modification example of the third embodiment is similar to the biosignal determination system 102 according to the third embodiment.
(Entire Process Flow)

Figure 31:
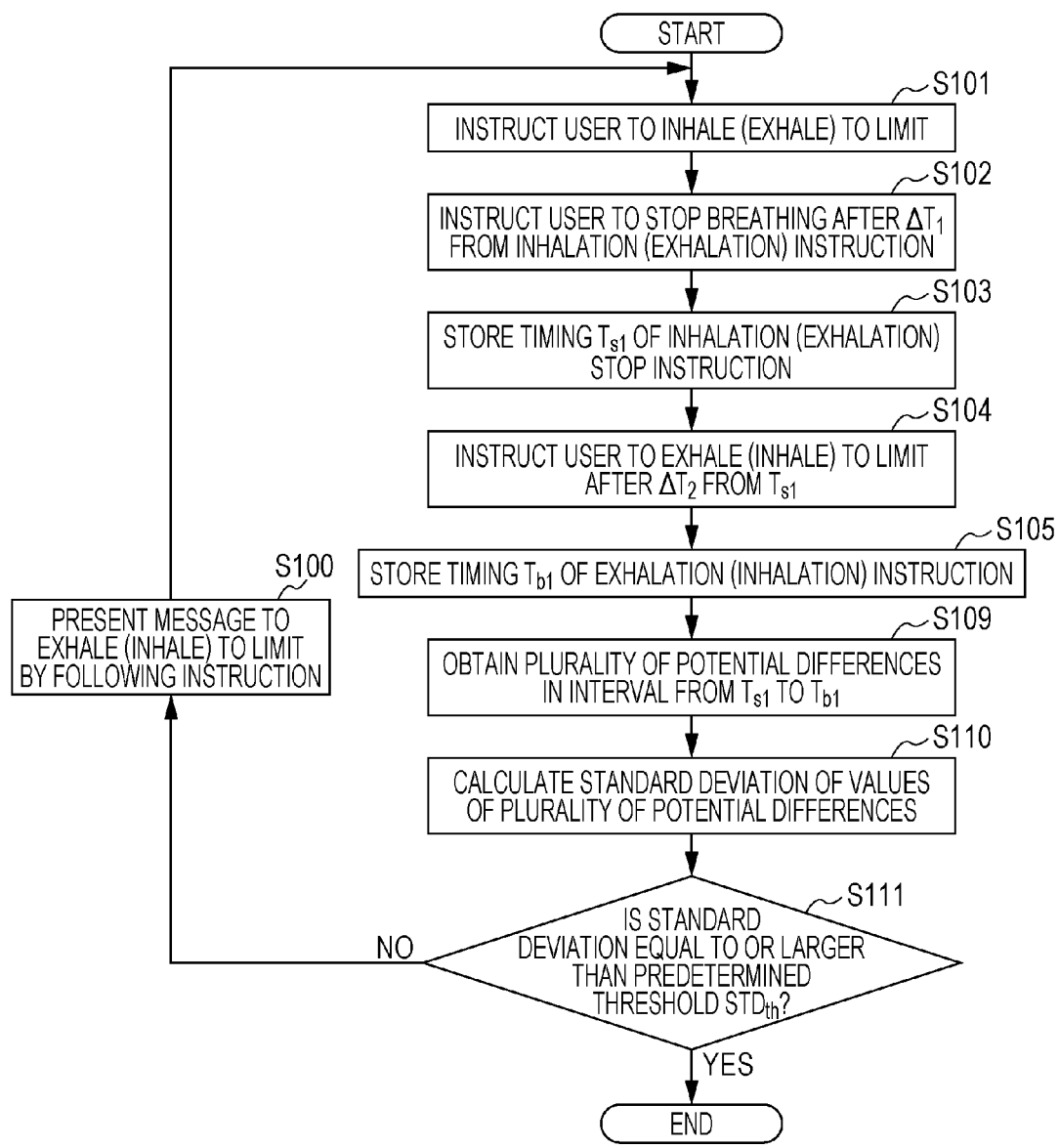
FIG. 31 is a flowchart of the procedure of a process of a biosignal determination system according to a first modification example of the third embodiment.

FIG. 31 depicts the procedure of the process of the biosignal determination system 103 of the present embodiment. The process flow is similar to the process flow depicted in FIG. 30 except steps S106 to S108 are removed.

In this disclosure, all or part of units and devices or all or part of functional blocks in the block diagrams of FIG. 15, FIG. 17, and FIG. 29 may be achieved by one or more electronic circuits including a semiconductor device, a semiconductor integrated circuit (IC), or a large scale integration (LSI). The LSI or IC may be integrated in one chip or may be configured by combining a plurality of chips. For example, functional blocks other than a storage element may be integrated in one chip. Here, those called an LSI and IC may be called differently depending on the degree of integration, such as a system LSI, a very large scale integration (VLSI), or ultra large scale integration (ULSI). A field programmable gate array (FPGA) programmed after manufacture of an LSI and a reconfigurable logic device capable of setting up reconfiguration of a junction relation inside an LSI or a circuit section in an LSI can also be used for the same purpose.

Furthermore, all or part of operations or functions of a unit, a device, or part of the device can be performed by software processing. In this case, software is recorded on one or more non-volatile recording media such as a ROM, optical disk, or hard disk drive. When the software is executed by a processor, the software causes the processor and its peripheral device to perform a specific function in the software. A system or device may include one or more non-volatile recording media, processors, and hardware devices for use, for example, interfaces.

According to the biosignal determination system of the present disclosure, it is possible to determine whether the user has fully inhaled or fully exhaled at the time of calibration of the amplitude and the respiratory volume. With this, the user can easily calibrate a respiration measuring device at home. The present disclosure can be applied to the field of checking a health condition at home or the like and ascertaining an exercise load state at the time of playing a sport.

What is claimed is:

1. A biosignal determining device comprising:
   an instruction output circuit which outputs a first instruction, a second instruction, and a third instruction, in this order, to a user,
      the first instruction prompting the user to perform an inhaling motion to an inhalation limit or an exhaling motion to an exhalation limit,
      the second instruction prompting the user to stop the inhaling motion or the exhaling motion, and
      the third instruction prompting the user to perform, to a limit, a motion opposite to the inhaling motion or the exhaling motion performed in response to the first instruction;
   a detection circuit which obtains a first cardiography representing a potential difference between two electrodes disposed on a chest of the user, the first cardiography measured between a time when the second instruction is outputted and a time when the third instruction is outputted, and detects a plurality of peaks included in the first cardiography; and
   a determination circuit which determines whether the user has performed the inhaling motion or the exhaling motion prompted in the first instruction to the inhalation limit or the exhalation limit, respectively, depending on whether potential values of the plurality of peaks are included in a predetermined range,
   further determines that the user has performed the inhaling motion or the exhaling motion prompted in the first instruction to the inhalation limit or the exhalation limit, respectively, when a standard deviation of values of potential differences between the plurality of peaks is equal to or larger than a first threshold, and determines that the user has not performed the inhaling motion or the exhaling motion prompted in the first instruction to the inhalation limit or the exhalation limit, respectively, when the standard deviation of the values of the potential differences between the plurality of peaks is smaller than the first threshold.

2. The biosignal determining device according to claim 1, wherein
   when the instruction output circuit outputs, as the first instruction, an instruction prompting the user to perform the inhaling motion to the inhalation limit, and the instruction output circuit outputs, as the third instruction, an instruction prompting the user to perform the exhaling motion to the exhalation limit.

3. The biosignal determining device according to claim 1, wherein
   when the instruction output circuit outputs, as the first instruction, an instruction prompting the user to perform the exhaling motion to the exhalation limit, the instruction output circuit outputs, as the third instruction, an instruction prompting the user to perform the inhaling motion to the inhalation limit.

4. The biosignal determining device according to claim 2, wherein
   the detection circuit further obtains a second cardiography representing a potential difference between two electrodes disposed on the chest of the user, the second cardiography measured after the time when the third instruction is outputted, and detects a plurality of peaks included in the second cardiography, and
   when the determination circuit determines that a value of at least one potential difference among the plurality of peaks in the second cardiography after the time when the third instruction is outputted is larger than a value of a potential difference of any of the plurality of peaks in the first cardiography between the time when the second instruction is outputted and the time when the third instruction is outputted,
   the determination circuit determines whether the user has performed the inhaling motion of the exhaling motion prompted in the first instruction to the inhalation limit or the exhalation limit, respectively, depending on whether the potential values of the plurality of peaks are included in the predetermined range.

5. The biosignal determining device according to claim 4, wherein
   the detection circuit further obtains a third cardiography representing a potential difference between two electrodes disposed on the chest of the user, the third cardiography measured after the time when the third instruction is outputted, and detects a plurality of peaks included in the third cardiography, and
   when the determination circuit determines that a value of at least one potential difference among the plurality of peaks in the third cardiography after the time when the third instruction is outputted is smaller than a value of a potential difference of any of the plurality of peaks in the first cardiography between the time when the second instruction is outputted and the time when the third instruction is outputted,
   the determination circuit determines whether the user has performed the inhaling motion or the exhaling motion prompted in the first instruction to the inhalation limit or the exhalation limit, respectively, depending on whether the potential values of the plurality of peaks are included in the predetermined range.

6. The biosignal determining device according to claim 1, wherein
when the determination circuit determines that the user has not performed the inhaling motion of the exhaling motion prompted in the first instruction to the inhalation limit or the exhalation limit, respectively, the instruction output circuit again outputs the first instruction.

7. A biosignal determining device comprising:
an instruction output circuit which outputs a first instruction, a second instruction, and a third instruction to a user,
the first instruction, the second instruction, and the third instruction are outputted in this order,
the first instruction prompting the user to perform an inhaling motion to an inhalation limit or an exhaling motion to an exhalation limit,
the second instruction prompting the user to stop the motion, and
the third instruction prompting the user to perform, to a limit, a motion opposite to the inhaling motion or the exhaling motion performed in response to the first instruction;
a detection circuit which obtains a first cardiography representing a potential difference between two electrodes disposed on a chest of the user, the first cardiography measured between a time when the second instruction is outputted and a time when the third instruction is outputted, and detects a plurality of peaks included in the first cardiography;
a processing circuit which generates respiratory information regarding respiration of the user in the first cardiography;
a determination circuit which determines whether the user has performed the inhaling motion or the exhaling motion prompted in the first instruction to the inhalation limit or the exhalation limit, respectively, depending on whether potential values of the respiratory information are included in a predetermined range, further determines that the user has performed the inhaling motion or the exhaling motion prompted in the first instruction to the inhalation limit or the exhalation limit, respectively, when a standard deviation of values of potential differences between the plurality of peaks is equal to or larger than a first threshold, and determines that the user has not performed the inhaling motion or the exhaling motion prompted in the first instruction to the inhalation limit or the exhalation limit, respectively, when the standard deviation of the values of the potential differences between the plurality of peaks is smaller than the first threshold;
a feature extraction circuit which extracts respiratory cycle information and amplitude information from a respiration curve obtained by the processing circuit;
an interface device which obtains information regarding gender, age, and height of the user;
a respiratory volume estimation circuit which estimates a respiratory volume of the user based on the information obtained by the interface device and the respiratory cycle information extracted by the feature extraction circuit and based on a predetermined mathematical expression; and
a calibration processing circuit which calibrates a relational expression of a respiratory volume and an amplitude of a respiration curve provided in advance, based on information regarding the respiratory volume estimated by the respiratory volume estimation circuit and the amplitude information extracted by the feature extraction circuit.

8. A biosignal determining method to be executed by a processor, the method comprising:
(a) outputting a first instruction, a second instruction, and a third instruction to a user,
the first instruction, the second instruction, and the third instruction are outputted in this order,
the first instruction prompting the user to perform an inhaling motion to an inhalation limit or an exhaling motion to an exhalation limit,
the second instruction prompting the user to stop the motion, and
the third instruction prompting the user to perform, to a limit, a motion opposite to the inhaling motion or the exhaling motion perform in response to the first instruction;
(b) obtaining a first cardiography representing a potential difference between two electrodes disposed on a chest of the user, the first cardiography measured between a time when the second instruction is outputted and a time when the third instruction is outputted, and detecting a plurality of peaks included in the first cardiography; and
(c) determining whether the user has performed the inhaling motion or the exhaling motion prompted in the first instruction to the inhalation limit or the exhalation limit, respectively, depending on whether potential values of the plurality of peaks are included in a predetermined range,
further determining that the user has performed the inhaling motion or the exhaling motion prompted in the first instruction to the inhalation limit or the exhalation limit, respectively, when a standard deviation of values of potential differences between the plurality of peaks is equal to or larger than a first threshold, and
determining that the user has not performed the inhaling motion or the exhaling motion prompted in the first instruction to the inhalation limit or the exhalation limit, respectively, when the standard deviation of the values of the potential differences between the plurality of peaks is smaller than the first threshold.

9. A biosignal determining method according to claim 8, wherein
in step (a), the first instruction prompts the user to perform the inhaling motion to the inhalation limit, and the third instruction prompts the user to perform the exhaling motion to the exhalation limit.

10. A biosignal determining method according to claim 8, wherein
in step (a), the first instruction prompts the user to perform the exhaling motion to the exhalation limit, and the third instruction prompts the user to perform the inhaling motion to the inhalation limit.

11. A biosignal determining method according to claim 9, further comprising:
(d) obtaining a second cardiography representing a potential difference between two electrodes disposed on the chest of the user, the second cardiography measured after the time when the third instruction is outputted, and detecting a plurality of peaks included in the a second cardiography, and
(e) determining whether or not a value of at least one potential difference among the plurality of peaks in the second cardiography after the time when the third instruction is outputted is larger than a value of a potential difference of any of the plurality of peaks in the first cardiography between the time when the second instruction is outputted and the time when the third instruction is outputted, wherein, in step (d), when the value of at least one potential difference among the plurality of peaks in the second cardiography is larger than a value of a potential difference of any of the plurality of peaks in the first cardiography, determining whether the user has performed the inhaling motion or the exhaling motion prompted in the first instruction to the inhalation limit or the exhalation limit, respectively, depending on whether the potential values of the plurality of peaks are included in the predetermined range.

12. A biosignal determining method according to claim 11, further comprising:
(f) obtaining a third cardiography representing a potential difference between two electrodes disposed on the chest of the user, the third cardiography measured after the time when the third instruction is outputted, and detecting a plurality of peaks included in the third cardiography, and
(g) determining whether or not a value of at least one potential difference among the plurality of peaks in the third cardiography after the time when the third instruction is outputted is smaller than a value of a potential difference of any of the plurality of peaks in the first cardiography between the time when the second instruction is outputted and the time when the third instruction is outputted, wherein, in step (f), when the value of at least one potential difference among the plurality of peaks in the third cardiography is smaller than a value of a potential difference of any of the plurality of peaks in the first cardiography, determining whether the user has performed the inhaling motion or the exhaling motion prompted in the first instruction to the inhalation limit or the exhalation limit, respectively, depending on whether the potential values of the plurality of peaks are included in the predetermined range.

13. A biosignal determining method according to claim 12, further comprising:
(h) when the user has not performed the inhaling motion or the exhaling motion prompted in the first instruction to the inhalation limit or the exhalation limit, respectively, outputting the first instruction again.

* * * * *